US006368276B1

(12) United States Patent
Bullis

(10) Patent No.: US 6,368,276 B1
(45) Date of Patent: Apr. 9, 2002

(54) DEEP PENETRATION BEAMFORMED TELEVISION

(76) Inventor: James K. Bullis, 1155 Pimento Ave., Sunnyvale, CA (US) 94087

( * ) Notice: Subject to any disclaimer, the term of this patent is extended or adjusted under 35 U.S.C. 154(b) by 0 days.

(21) Appl. No.: 09/448,023

(22) Filed: Nov. 23, 1999

(51) Int. Cl.[7] ................................................. A61B 8/00
(52) U.S. Cl. ....................................................... 600/437
(58) Field of Search ................................ 600/437–447, 600/407, 425, 473; 128/916; 348/128, 131; 356/612; 367/7, 11, 130; 73/620–627

(56) References Cited

U.S. PATENT DOCUMENTS

| 4,512,197 A | * | 4/1985 | von Gutfeld et al. ......... 73/643 |
| 4,694,434 A | * | 9/1987 | von Ramm et al. ............. 367/7 |
| 5,086,775 A |   | 2/1992 | Parker et al. ........... 128/660.01 |
| 5,103,129 A | * | 4/1992 | Slayton et al. ............... 310/335 |
| 5,598,206 A |   | 1/1997 | Bullis .......................... 348/81 |
| 5,808,967 A |   | 9/1998 | Yu et al. ...................... 367/91 |
| 5,814,731 A | * | 9/1998 | Alexander et al. ............ 73/644 |
| 5,901,708 A | * | 5/1999 | Chang et al. ................ 128/916 |
| 5,966,169 A |   | 10/1999 | Bullis .......................... 348/81 |
| 5,999,836 A | * | 12/1999 | Nelson et al. ............... 600/407 |

OTHER PUBLICATIONS

Fatemi and Greenleaf, Ultrasound–Stimulated Vibro–Acoustic Spectrography, Apr. 3, 1998 pp 82–85.

* cited by examiner

Primary Examiner—Marvin M. Lateef
Assistant Examiner—Ali M. Imam

(57) ABSTRACT

The invention is a new system for deep penetration medical imaging in a comprehensive medical system. Imaging is based on beamformed television methods that utilize orthogonal arrays to image three dimensions with high resolution. The comprehensive medical system is a flexible apparatus that includes detection, diagnostic, and treatment capabilities. Deep penetration operation in attenuating tissue is enhanced by semi-collimated beams which improve signal to noise ratio. The semi-collimated beams improve control of the field of view and simplify signal processing. Embodiments include additional features to enhance deep penetration imaging and make it practical.

36 Claims, 25 Drawing Sheets

DEEP PENETRATION BEAMFORMED TELEVISION

BACKGROUND OF THE INVENTION

1. Field of the Invention

Figure 1:
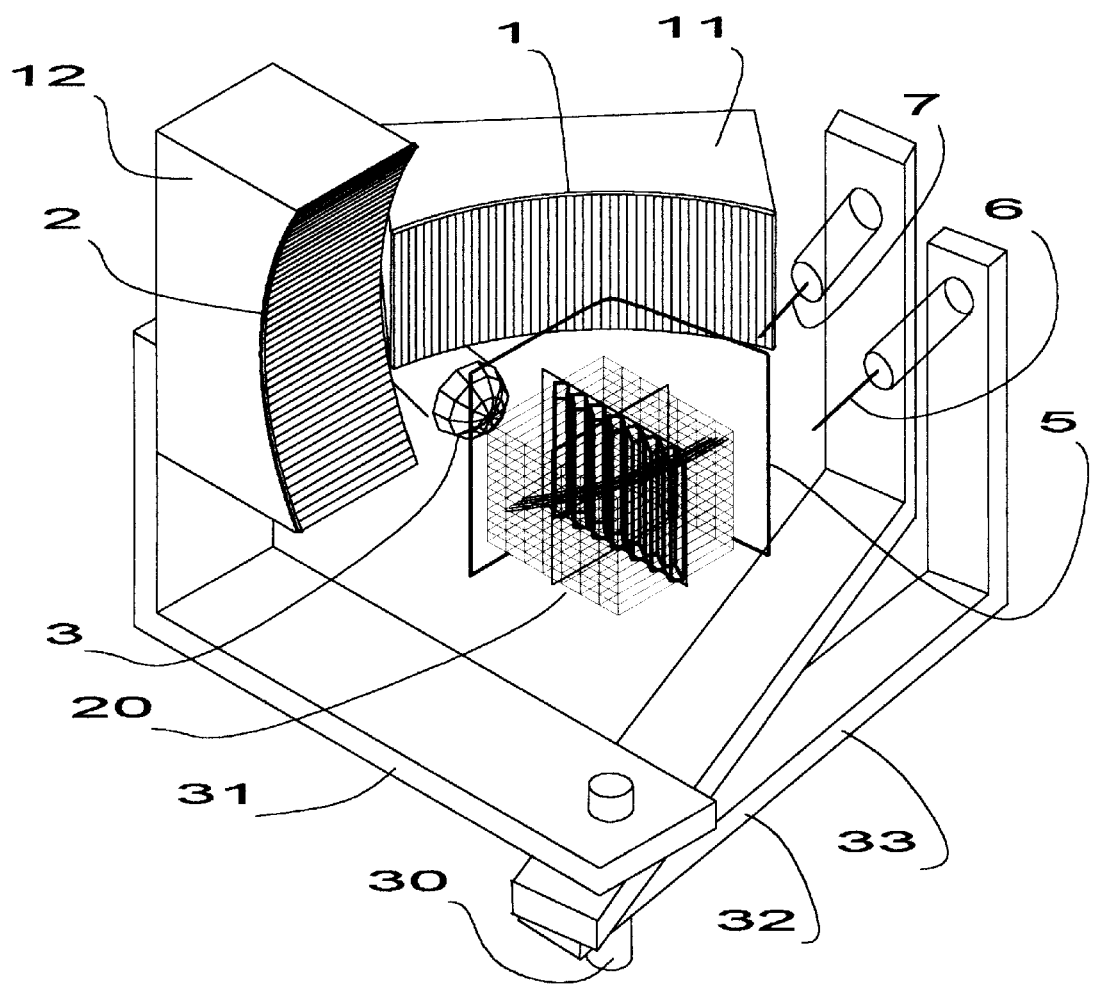

The invention relates to creating images by transmitting signals and sensing the effect of objects in the field of view on the signals.

2. Description of the Prior Art

Using available light and optical methods, popular video cameras and television receivers produce high quality pictures in the format of human vision in real time. Beamforming techniques emulate optical methods by transmitting and receiving signals with transducer arrays and processing such signals. These techniques are especially important where light fails to penetrate effectively. However, it is difficult to match quality of familiar television system images using such beamforming methods.

The beamformed television method, U.S. Pat. No. 5,598,206 (January 1997) Bullis, approaches this goal with a practical hardware configuration. It provides visual format images at a frame rate that enables motion viewing. A three dimensional variation, U.S. Pat. No. 5,966,169 (October 1999) Bullis, emphasizes a practical method to achieve fine grain range resolution to enable viewing from any arbitrary perspective. The three dimensional block acquisition enables tissue tracking, guidance of therapeutic instruments and monitoring of healing.

Beamformed television, as disclosed in U.S. Pat. No. 5,598,206 (January 1997) Bullis, used a pair of orthogonal linear arrays. One array was for transmitting signals and one array was for receiving signals. A system of intersecting beams resolved a scene, as required for visual format imaging. This method requires that beams be narrow in one dimension and wide in the other dimension. These beams were described as fan beams. They are asymmetrical about the beam axis. The linear array configuration efficiently produces such beams. However, efficient formation of a useful field of view leads to transducer However, efficient formation of a useful field of view leads to transducer spacing, on center, also called pitch, that results in grating lobe effects. The general idea was to utilize one dimension of each array to resolve one angular, or cross range dimension, of a scene and the other dimension of that array to suppress grating lobes. The two arrays together resolved both cross range dimensions and limited the field of view in these dimensions. A variation involved limited steering that moved the field of view.

Although the directive effects of transmit array and receive array are described in beam pattern terms, there are important differences in the actual beamforming processes. Receive beamforming simply means adjusting for arrival time and adding signals to focus the collection of received signals. Simultaneous receive beamforming is based on the same set of received signals, except differing sets of arrival time adjustments are applied to sense in different directions and at differing focal zones. With sufficient computing power, all possible receive beam directions and focal zones can be sensed in a single transmit and receive event. Transmit beamforming means arranging signals to cause signals to be transmitted in a time relationship that causes focus in a selected direction and focal zone. Parallel transmit beamforming degenerates unless there is a way to separate signals. However, a need for rapid acquisition requires a similar parallel process.

A coding method was utilized. This enabled simultaneous excitation at different angles and at different focal zones. This was the needed complementary counterpart to simultaneous receive beamforming.

A combination of these complementary processes, operating with arrays that are orthogonal, provides highly efficient resolution in two cross range, or angular, dimensions. The resolving system can be accomplished with arrays that are straight line arrangements of elements that are called linear arrays.

It was found that grating lobe suppression could be accomplished by utilizing the width dimension of the linear arrays. A widening method was disclosed that utilized multiple transducers in a transverse arrangement relative to the line of the array. A specified alternative was to widen the transducers in the transverse direction. These widening provisions tended to improve power handling and gain of the system but the disclosure, U.S. Pat. No. 5,598,206 (January 1997) Bullis, primarily discussed the grating lobe suppression effects. This prior disclosure noted that beam descriptions were inexact, especially in the near field. Thus, the possibilities of widening were not fully explored.

Three dimensional systems, U.S. Pat. No. 5,966,169 (October 1999) Bullis, were made practical by the step chirp method for resolving the range dimension of the field of view. This was found to be possible to operate in combination with the coding method and other features of the preceding invention, U.S. Pat. No. 5,598,206 (January 1997) Bullis.

The three dimensional method made medical imaging a compelling development project because it solved the fundamental problem of wide slice thickness that is inescapably the result of a narrow aperture that is the width dimension of the conventional, single array systems. The orthogonal array method was a leap ahead of industry efforts that are based on "1.5D" methods. But it was a completely electronic scanning system. The industry tendency is to utilize the conventional architecture with mechanical scanning apparatus to acquire a three dimensional block of image data.

Because the architecture of the orthogonal array applications is so different from the conventional form, it became useful to use a differentiating term. Instead of calling this technology ultrasound, the name orthosound was chosen. This emphasizes the orthogonal relationships in the architecture and helps to convey that this is not a small improvement to the familiar form, but is a major change in system architecture with very substantial benefits.

However, there are deep penetration issues with medical imaging using orthogonal array technology. In the terminology of this disclosure, these issues are categorized as (1) signal to noise ratio effects, (2) signal to clutter ratio effects, and (3) waveform and wave-front distortion effects. Signal to noise ratio can be improved by increasing transmitted signal level. Signal to clutter ratio stays the same if transmitted signal level is changed. Both of these can be improved by improving resolution where signal to noise ratio benefits from improved gain and signal to clutter level improves because clutter sources are excluded from a given resolution cell. Clutter is distinguished from artifacts. Clutter is a general background level that shows no recognizable shape. It comes from reflection signals that overpower the system capability to discriminate. Artifacts are similar except they are objects in the image that are recognizable representations of real objects that are incorrectly brought into the field of view. A pixel of a display represents the composite signal strength of the scattering sources that are within an associated voxel. A voxel is a volume resolution cell. Distortion effects degrade the signal processing operations.

The important qualities of a system begin with the capability to resolve a voxel. The degree of noise and clutter that are represented in the voxel also determine system capability. Contrast must be sufficient that objects can be discerned in the presence of interference by the noise and clutter. However, a well resolved set of voxels can represent objects such that these objects can be recognized by a pattern that approximates their shape. This is a powerful system gain effect. Distortion of signal waveform and wave-front shape modifies the capability to resolve a voxel, causing reduction in signal level and reduction in capability to reject interference. Distortion effects also disturb patterns so that shapes are not adequately recognizable.

The term real time describes timeliness of the imaging operation, but it is not clearly or consistently used. It definitely does not mean a delay in processing such as developing a film. For viewing of moving objects, it means a frame rate comparable to television. It may mean that it is soon enough to allow adjustment of system parameters and re-examination of a patient without a return visit. Although not precise, it is a critical measure of the usefulness of a system in any given application.

Deep penetration applications result in deterioration of image quality or timeliness. The background of the present invention includes previous disclosures as well as limitations therein. It also includes capabilities from other fields that can be utilized and capabilities and methods that are utilized in the popular conventional systems.

Previous disclosures, U.S. Pat. No. 5,598,206 (January 1997) Bullis and 5,966,169 (October 1999) Bullis, used approximations in discussing near field effects. These effects are significant to medical imaging configurations so the near field beam shapes must be more precisely addressed.

Methods are well known to make transducers that are sub-divided so that a transducer is actually a collection of transducers that are driven with a common signal line. This is commonly done to free the transducer motion in a transverse direction so that displacement in the desired direction can occur by material distortion rather than compression. Diamond dicing saws are known tools for subdividing piezo-electric transducers. They are also used to fabricate arrays of multiple transducers by cutting up a larger piece of piezoelectric material. Various means are known for making electrical connections, include soldering, ultrasonic welding, and conductive composite materials.

It is well known to improve signal to noise ratio by integrating the results of repeated transmission. Such repeated operations of a given sensing system are considered obvious. This measure carries a penalty of slowing the frame rate of the system.

The patent U.S. Pat. No. 5,598,206 (January 1997) Bullis disclosed use of signal tones of finite duration as codes. This method provides a resolution that is inherent to the code form. With simple tone codes, the time resolution is equal to the duration. This effect can be thought of as a range gate effect where a particular resolution increment is acquired by the receiver system and becomes a sample of the signal. This signal sample represents reflected signal from a limited range extent. This previous patent did not address the ramifications of deep penetration imaging in highly attenuating tissue though it did note the trade-off between tone code time duration and the number of codes that could be used in the available system bandwidth.

Another design issue in deep penetration applications is that of maintaining the range resolution effectiveness at depth. The general practice in the medical ultrasound industry is to use simple, short pulses to ensonify the field of view. The equivalent frequency domain representation of such short pulses is a very broad band of energy. In deep penetration systems, the natural attenuation process will effectively filter out most of the energy, leaving the system with a reduced band of energy. This will result in a much degraded received pulse width.

A step chirp method of signal processing was previously disclosed, U.S. Pat. No. 5,966,169 (October 1999)Bullis, which provides fine grain range resolution using simple frequency codes. This method specifically included the capability to adjust for variations in frequency response of the system. However, it did not address the severe variations of attenuation as a function of frequency.

The medical ultrasound industry has been actively pursuing methods called harmonic imaging, that involve transmitting signals from an array on a frequency and receiving signals that are twice the frequency. Penetration depth is benefited since the transmitted signals are at a lower frequency so that the outward one way path is significantly less attenuated than the return path.

The harmonic received signals are not the product of simple reflection in a linear system. The observed fact of such harmonic signals indicates that processes take place that are related to the nature and condition of the tissue. Such effects are also observed in materials. Various mechanisms for generation of these harmonic like signals are possible, one of which is a nonlinear effect that is similar to passive intermodulation distortion in communication antenna reflectors. Greenleaf, *Science,* Apr. 3, 1998, Volume 280, pp.82–85, shows the effect of two separate frequencies that produce the sum and difference frequency signals. It appears that U.S. Pat. No. 5,086,775, (February 1992) Parker et. al., is also addressing this effect.

Contrast enhancement is widely known in the industry. This involves injecting suitable materials into the blood stream so that the contrast between the blood path and surrounding tissue is more visible in images.

Most commercial ultrasound systems implement beamforming in only one dimension. That resolves the azimuth, or horizontal, cross range dimension. These devices produce an image by using the range dimension information so that a visual format display is not possible. This is an adaptation of the general architecture of most radars and sonars, whether used for detection or imaging. This simple architecture is efficient, but it fails to effectively limit the elevation beamwidth, thus providing only crude capabilities to show small details and very coarse capability to locate objects in the elevation, or vertical, dimension.

Adaptation of the simple radar and sonar architecture is especially problematic because of the extreme, three dimensional clutter environment that is encountered in medical imaging. The fact that the elevation, or vertical, dimension is not resolved beyond the field of view limitation of the slice thickness means that the volume resolution cell, or voxel, is crudely formed. This voxel is greatly elongated compared to its azimuth and range dimensions. This means that all clutter signals from sources within a voxel are added to the desired signal from a small object that is within the voxel. An appropriate system design matches the voxel to the approximate size of the smallest object that needs to be sensed or the smallest degree of detail that needs to be discerned.

In spite of this limited architecture, much progress has been made in ultrasound imaging. Powerful computing machines are made in compact form. A wide range of transducer array forms are available and a typical system has several on hand to be used as needed. These are plugged in to a computing console, one at a time. Such arrays are simply called transducers in the terminology of the medical imaging industry.

Transducer array fabrication methods are highly refined in this industry and very small, very high frequency arrays are efficiently manufactured. Such fabrication methods are represented in U.S. Pat. No. 5,808,967 (September 1998) Yu, et. al. This disclosure also discusses methods of transmitting and receiving axially symmetric beams from a mosaic planar array form, with interconnection methods to make elements electrically independent.

Only primitive forms of three dimensional imaging are currently accomplished by mechanical scanning of instruments based on the conventional, single array, architecture. Not only is this a slow way to scan, but the ultimate results are fundamentally flawed by the voxel formation capabilities of the instrument utilized.

In spite of the architectural flaw and lack of three dimensional capability, much progress has been made in ultrasound imaging. Powerful computing machines are made in compact forms. A wide range of transducer forms are available and a typical system has several on hand to be plugged in and used as needed. These are plugged in to the console, one at a time.

Known fabrication and switching methods are represented in U.S. Pat. No. 5,808,967 (September 1988) Yu, et. al. Where methods are disclosed for making transducers electrically independent and independently transmitting and receiving of axially symmetric beams.

This architecture is also poor in supporting navigation processes. The lack of accurate position fixing capability in the elevation angle dimension is a basic failing of this architecture whether it be to guide airplanes, torpedoes, or the insertion of instruments to treat diseases.

X-ray equipment is utilized for breast cancer screening. This imaging modality is also a two dimensional process that collapses a three dimensional volume onto a two dimensional film or other form of detector. It forces the examiner to try to see through many layers of tissue. The standard of early detection in this field is to find a tumor when it is about 0.5 cm. Success rate for finding smaller tumors does not seem to be a subject of statistical studies.

A radiologist typically looks at x-rays from successive examinations. It is also common practice to compare images obtained with different imaging modalities. Examination of vast quantity of images becomes burdensome to radiologists. Computer methods exist to handle digitized x-ray images, whether these are acquired by scanning film or by direct electronic sensing.

There are software means to track detailed movements in dynamic environments such as radar systems operating against a large number of detectable targets, some hostile and some friendly. Such software requires three dimensional sensing if the environment is complex. There are also methods of comparing natural images and variations therein. Wavelet methods are known to be useful in allowing for natural variations in such comparisons.

There are existing methods and new methods being developed to eliminate diseased tissue, once it is located. Some of these methods have the capability to be highly selective in their effect so as to eliminate only the diseased parts. These include locally effective drugs, energy sources that burn out the diseased region, and precise surgical methods. A prior art method that involves a locally effective injection is disclosed in U.S. Pat. No. 5,902,582 (May 1999) Hung. To effectively insert an instrument, such as a needle, it is highly beneficial to know the exact angle to point the needle relative to the insertion point and then to be able to follow the movement of the needle tip as it approaches the desired spot. This type of guidance is not available with prior art imaging modalities.

It is common practice to monitor the progress of patients after treatment for disease.

It is common practice to efficiently treat early forms of skin cancer where the problem is observed and treated in a single office visit.

Comprehensive military systems are known that sense and track threat targets and friendly targets, control and guide weapons, and assess results.

Referenced documents, in entirety, are incorporated herein. They contribute to the description of the present invention, but in case of conflict, the present document takes precedence.

OBJECTS

A general object is to enable deep penetration in attenuating bodies and to rapidly produce three dimensional images that can be efficiently processed to give complete perception of the three dimensional block of information.

An object is to provide a complete three dimensional imaging system for medical ultrasound imaging in human or other living bodies.

An object is to provide a comprehensive medical system apparatus with integrated capability to arrange image equipment in a variety of configurations and control operating modes to carry out a sequence of detection, diagnostic, and therapeutic procedures in a single on-line session.

An object is to provide hand held transducer array systems that allow practitioners to move imaging device to a chosen location on a patient's body.

An object is to provide a small footprint sensor that will enable viewing access between ribs.

An object is to replace x-ray imaging devices with ultrasonic imaging devices.

An object is to provide imaging over the dimension of velocity.

An object is to provide improved power intensity levels and receive sensitivity.

An object is to provide improved signal to noise ratio.

An object is to provide a simplified, transverse plane, flat scanning capability.

An object is to provide superior slice imaging.

An object is to reduce the risk of fracturing transducer elements in normal use.

An object is to reduce size of the entry region into the body.

An object is to minimize acoustic wave energy in the body.

An object is to minimize peak acoustic pressure in the body.

An object is to suppress clutter in images.

An object is to correct for refraction effects.

An object is to enable aberration correction.

An object is to reduce pulse distortion in time domain forms of reflected signals, and correspondingly improve range resolution.

An object is to enable simplified range gating hardware.

An object is to provide a research tool to investigate the scattering levels and harmonic content of such scattering for various types of human tissue.

An object is to enable imaging with low acoustic power intensity levels to prevent damage to the subject of examination.

An object is to minimize thermal losses in the transmitting transducer.

An object is to control clutter interference.

An object is to provide high resolution in the range dimension in environments where there is strongly differing attenuation over the frequency band.

An object is to provide diagnostic information related to tissue characteristics and condition.

An object is to utilize contrast enhancement substances to enable deeper penetration imaging and to enable high resolution viewing and to enhance sensitivity to motions such as blood flow motion.

An object of the present invention is to image the velocity field of moving particles in bodies.

An object is to provide overlay capability to enable comparison of successive examinations and comparison with other imaging modality results.

An object is to track tissue changes so as to distinguish development of diseases.

An object is to utilize computers in examination of large quantities of images.

An object is to guide disease treatment procedure.

An object is to provide industrial process inspection capability that does not involve destruction of the object.

An object of this present invention is to provide a complete three dimensional imaging system for underwater exploration or other underwater operations.

An object of this present invention is to provide a ground penetrating radar system that has sufficient resolution to distinguish between objects of interest and natural objects.

An object of this present invention is to provide an air acoustic imaging system, with optional capability to penetrate the ground to search for articles of interest.

An object of this present invention is to enable real time navigating of mobile operations such that high speed operations are enabled.

An object of the present invention is to enable dynamic guidance of systems including pointing information in two angular dimensions.

An object is to emulate the effectiveness of bats and other animals in detecting and homing on objects and avoiding obstacles in high speed flight.

Further objects of the present invention will become apparent from a consideration of the drawings and ensuing description.

SUMMARY OF THE INVENTION

A system has been invented that provides deep penetration, collimated, three dimensional, real time, ultrasonic imaging of the internals of the human body with diagnostic sensing features and treatment enabling features. The apparatus is a flexible arrangement of arrays and associated medical equipment, with means to select operating configurations and to control operating parameters. Because the sensing configuration makes extensive use of orthogonal arrangements and to distinguish it from conventional ultrasound technology, this new technology is called orthosound imaging.

A powerful parallel computer architecture enables use of a variety of transducer array forms and signal systems. As with conventional ultrasound apparatus, arrays are plug in devices that are changed to fit needs.

Orthosound is a combination of prior beamformed television inventions, U.S. Pat. No. 5,598,206 (January 1997) Bullis and U.S. Pat. No. 5,966,169 (October 1999) Bullis with new features that provide deep penetration capabilities in environments where signals are strongly attenuated by the medium of propagation. The new features include a wide array configuration with sub-divided elements, switching to configure transmit or receive configurations, bracket gating, attenuation compensation, and signal modulation methods. The sub-divided wide array method provided geometric beam control, including a fully collimated capability, that has a variety of unexpected benefits. The new features not only improve signal strength, they also suppress interference and give improved diagnostic capabilities. Medical treatment features are enabled and enhanced at greater depth.

Like the previous inventions, a transmit array and a receive array are oriented to resolve two cross range dimensions and a sparse array method efficiently forms a desired field of view. These arrays are arranged to be orthogonal to each other, and each produces respective beams that are orthogonal to each other. This new architecture incorporates a transmit beam segment coding method that enables rapid acquisition and a step chirp method that enables efficient range resolution. The system includes a capability to choose between a variety of array forms and signal operations to meet examination requirements.

An improved penetration capability is achieved with wide arrays that produce semi-collimated beams. Such an array has superior power handling capabilities and improves signal to noise ratio.

Semi-collimated beams are beams that are collimated in one transverse dimension in the region of the field of view and focused in the other transverse dimension. An orthogonal combination of two semi-collimated beam systems produces a system function that is fully collimated. Flat arrays produce a rectangularly collimated system and the field of view is a rectangular block. This enables rectangular displays without adjustment by image data processing.

Rectangular collimation improves clutter rejection capabilities in conjunction with the fine grain range resolving capabilities of the signal system. An operator has the flexibility to tune the bistatic angle, which is the angle between the two arrays, to emphasize this effect.

A further benefit of rectangular collimation is a refraction control capability in water bath or water stand off implementations. A flattening window made of thin plastic material is a system component that causes the transition from water to human tissue to occur over a planar surface. In conjunction with this tool, the arrays are oriented so that the straight line elements of both arrays are parallel to the planar surface. Time delay adjustments for transmit signals and receive signals effectively correct the refraction.

Since the array width dimension is flat the array can be curved in the other dimension without requiring a doubly curved surface. This is a more easily manufactured configuration that provides an orientation of individual transducer elements to better encompass the field of view.

The collimated concept is made possible by near field effects that shape beams at ranges short of where diffraction effects become important. In this near field, beam shapes are determined by the shape of the radiating aperture and signal timing. To know the size and shape of an active wavefront is to know the shape of the beam that it is to subsequently trace out. An alternate semi-collimated transducer array form is characterized as causing cylindrical collimation in one dimension. Cylindrical collimation causes a field of view that diverges or converges with range. Cylindrical collimation involves concave or convex radiating wavefronts. Radiating surfaces are approximately shaped like the wavefront or they are shaped like a section from the inner or outer surface of a cylinder with electrical time adjustment to impart the respective wavefronts. In general, radiating surfaces are quite arbitrary since the electrical system can adjust for many physical shapes. Plug-in arrays utilize combinations of rectangular and cylindrical semi-collimated methods.

Cylindrical collimation of either type does not give the rectangular field of view benefits. The concave form modifies power handling and causes curved focal zones that enhance the interaction with range resolving features to reduce sidelobe effects. Convex wavefronts allow thinner transducer arrays for shape and size restricted applications.

Returning to the primary array form that is straight line elements arranged along a cylindrical surface, it was found to be useful to utilize a known process of sub-dividing transducer elements to improve radiating surface displacement. It was found that long, thin, transducers could also be sub-divided into sub-elements so as to make transducers more durable. It also improves electrical interfacing. Here the sub-elements are separately connected to amplifiers that operate in parallel. Parallel amplifiers utilize the same signal so that a single signal channel is still sufficient.

An increase in the number of amplifiers adds cost, but an advantage of sub-divided elements and separate amplifier circuits is that it makes possible a new diagnostic mode of operation, at low additional cost, where the field of view is subdivided by switching amplifiers on or off. Sub-beams are selectively created. The sub-elements individually have semi-collimated properties. Sub-beams are like the system semi-collimated beams, only thinner. This can be done with either or both transmit amplifiers and receive amplifiers. These are on-line system adjustment options that do not require changing transducers. It will significantly reduce effects of sidelobes from the opposite array. This provides a highly sensitive mode of operation that can be applied for diagnostic purposes when suspicious things are seen in a larger image.

Programmable range resolving modes include simple pulse, step chirp, and gated continuous wave. New combinations of these modes have significant benefits. Simple step chirp operations are not compatible with transmit beam segment coding methods.

Bracket gating is a hybrid combination of simple pulse methods and step chirp methods. In this hybrid method, system range resolution is ultimately determined by the step chirp process, but an earlier stage of coarse range resolution is provided by the bracket gate. Bracket gating is particularly important for deep penetration applications where short range signals are overwhelmed by long range signals. Bracket gating involves tones that are stepped in frequency, but tone duration is greatly reduced such that a short duration sampling window fully accepts reflections only from a single range and excludes earlier and later returns. The rejection effectiveness is gradual, but for return signals that completely miss the sampling window, the rejection is very strong. This limits clutter effects prior to analog to digital conversion of received signals. A short bracket gate reduces the unambiguous range to be resolved by the step chirp process, so it reduces the number of steps that must be used in that process. Tone duration is adjusted so that a balance is achieved between interference effects of clutter and interference effects of noise.

However, the use of narrow bracket gates leads to signal processing complexity in signal processing where coding is used to simultaneously acquire different focal zones. This situation is much improved by a staggered burst transmission program where transmit code tones are timed so that all codes arrive back at the receiver at about the same time. Even though the stagger causes overlap for differing ranges, it is only nominal overlap since wide aperture effects and field of view width cause tones to arrive that are spread out in time. The various ranges and angles represented by such tones are needed for effective signal processing. A sliding processing window is used to effectively capture full tones. This prevents poor quality decoding and poor quality receive beamforming.

Bracket gating is especially important in enabling small footprint array systems where short stand-off operation is desired. The step chirp process can still be utilized in this arrangement because of the bracket gate.

Another new feature is a modification of the step chirp process to prevent degradation of range resolution in deep penetration applications. The transmit signals are adjusted for each step of the step chirp to give increasing amplitude as frequency increases. This process compensates for the extreme variation of attenuation over the frequency band causing a received signal spectrum that transforms to a short pulse to enable well defined range resolution increments. In simple pulse mode operation, spectrum modification is applied to transmit pulses and signal samples are arranged in transmit signal memory to give a similar effect.

Deep penetration is enhanced by use of modulation effects. Modulation is a process that produces signals that have frequencies that are different from transmitted signal frequencies. This effect enables lower attenuation return paths. It also gives diagnostic capabilities since the modulation effects are variable depending on tissue condition. Both arrays of the original orthogonal configuration are operated as coded transmit systems and the difference frequencies arise at intersections of beams.

Three dimensional capabilities of the imaging system enable highly perceptive pattern recognition capabilities of the human eye and brain.

Where needed, the three dimensional capabilities also enable highly precise navigation and control of instruments to carry out treatment procedures.

Signal processing is carried out using parallel computing hardware with a network switch that enables parallel, high speed transfer of information between computers at high speed.

Image signals are displayed for direct evaluation, image data is processed to optimize viewing sensitivity, therapeutic measures are guided, and the system configuration is optimized in a comprehensive medical system that enables a sequence of detection, diagnosis, and therapeutic procedures in a single office visit.

DESCRIPTION OF THE PREFERRED EMBODIMENT

The scope of the invention should be determined by the appended claims and their legal equivalents and not by the examples and variations given.

This disclosure is written in terminology for the system design engineer who is knowledgeable in a wide range of disciplines within the general electronic and physics professions. A variety of specialists is typically required to produce the detailed hardware, depending on the application. Construction involves separate disciplines that include skills in transducer design and manufacturing, computer architecture, analog and digital circuit design, and software.

DRAWINGS

FIG. 1—a comprehensive medical system for deep penetration imaging, diagnosis, and treatment.

Figure 2:
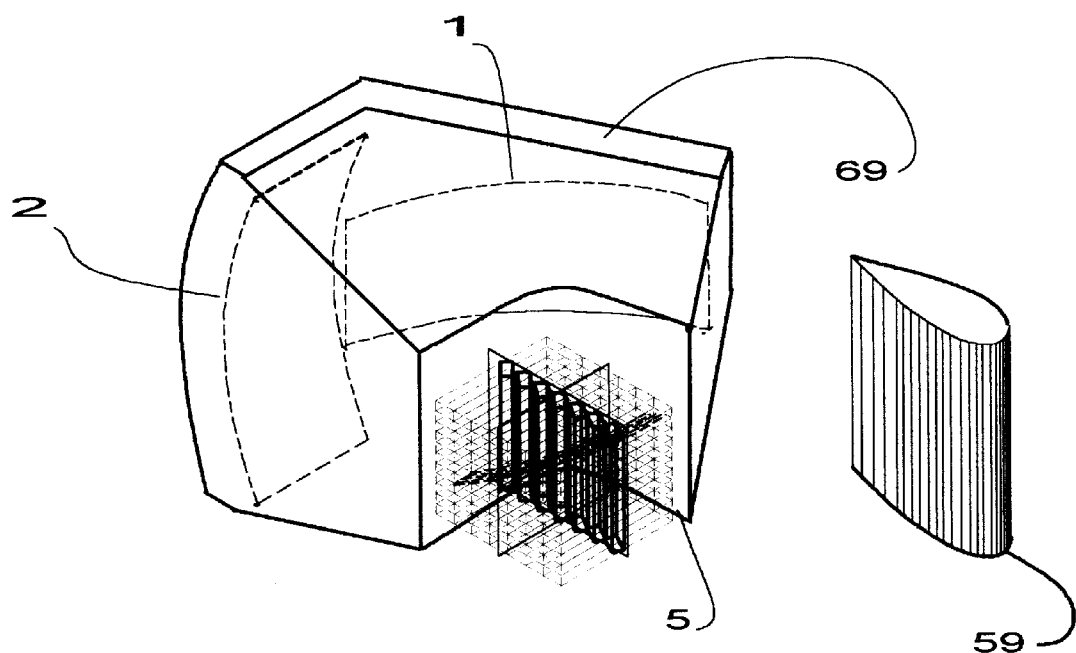

FIG. 2—a hand held enclosure containing arrays and fluid, and stand-off cushion.

Figure 3:
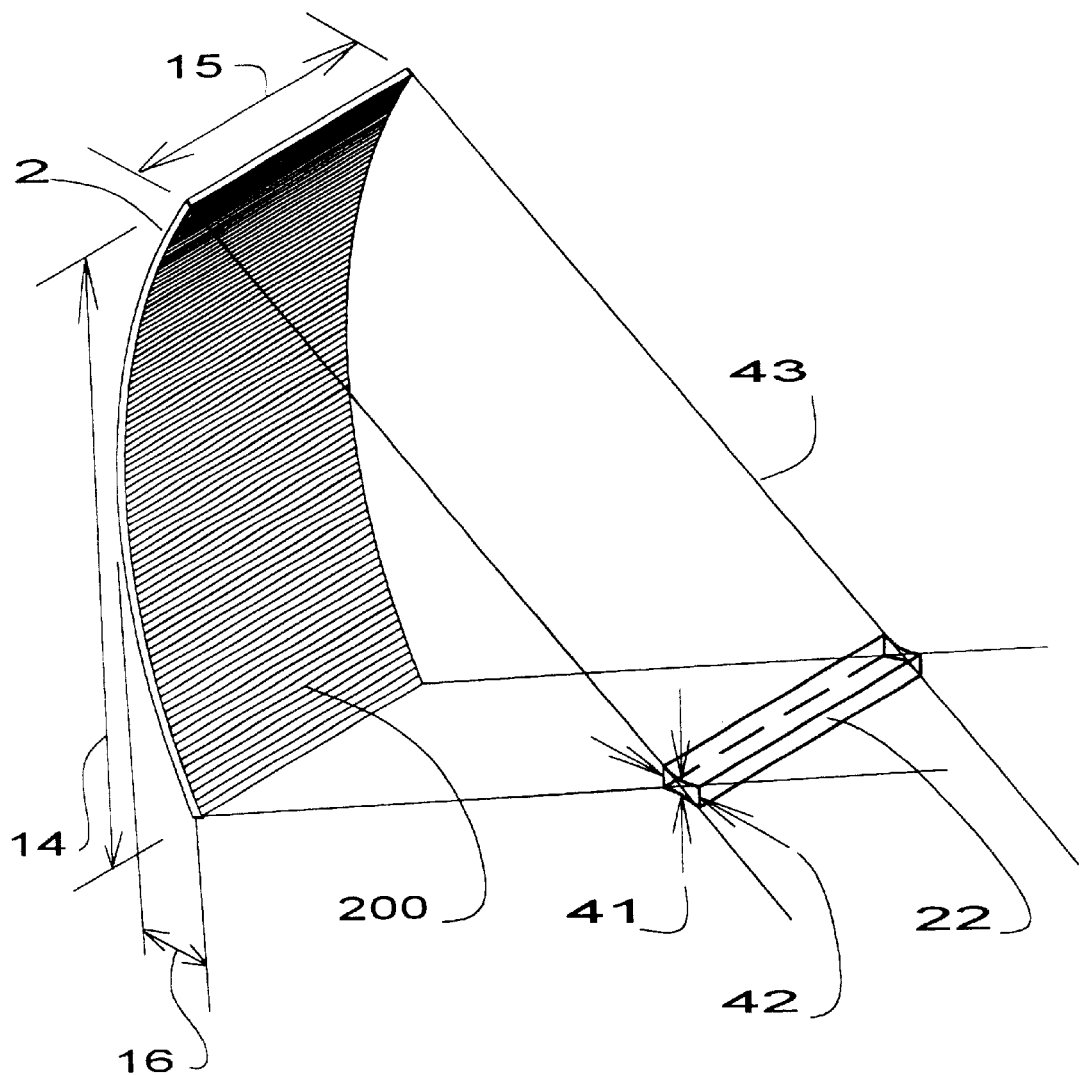

FIG. 3—a receive array and a semi-collimated receive beam segment.

Figure 4:
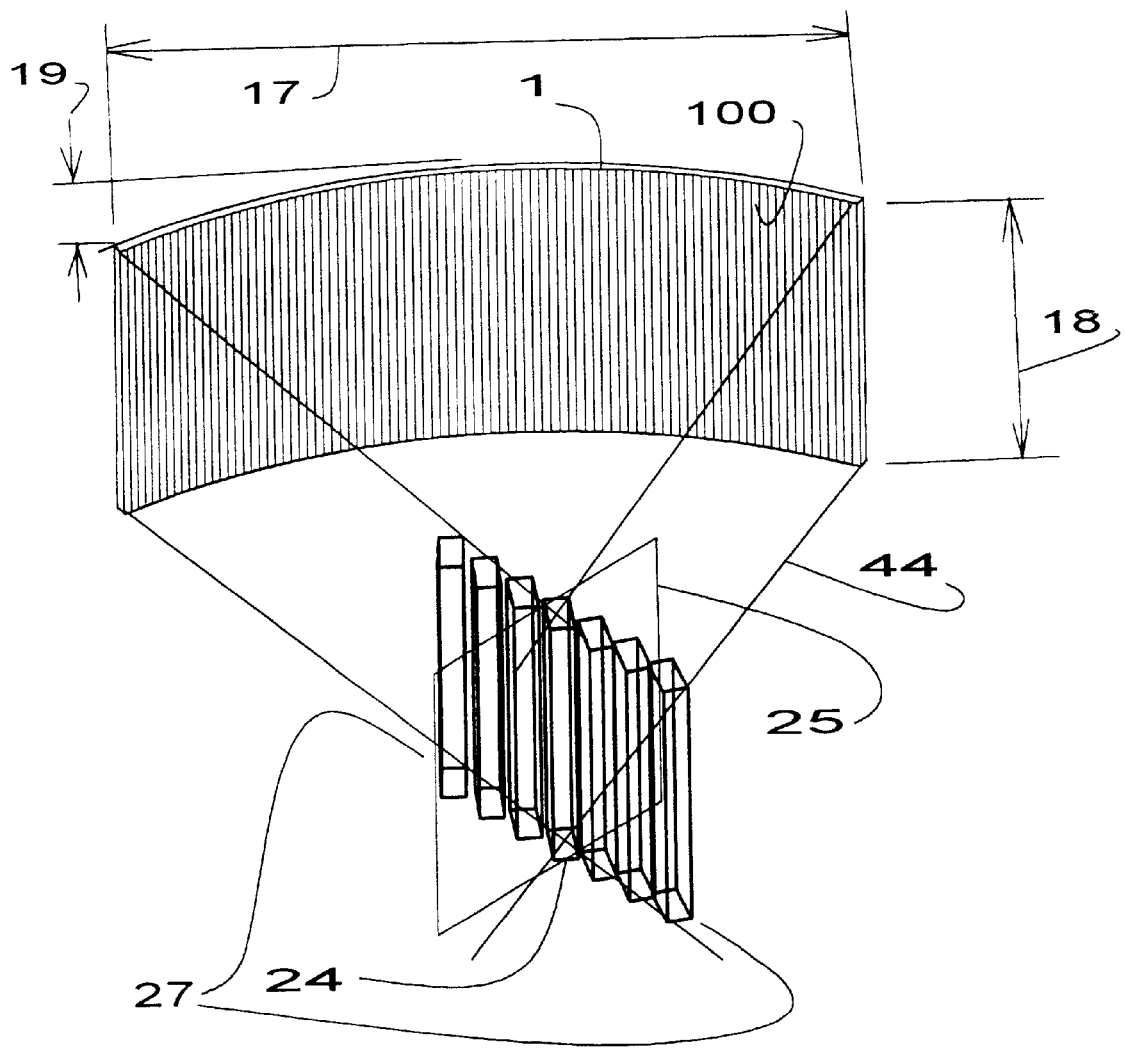

FIG. 4—a transmit array and a set of coded, semi-collimated, transmit beam segments.

Figure 5:
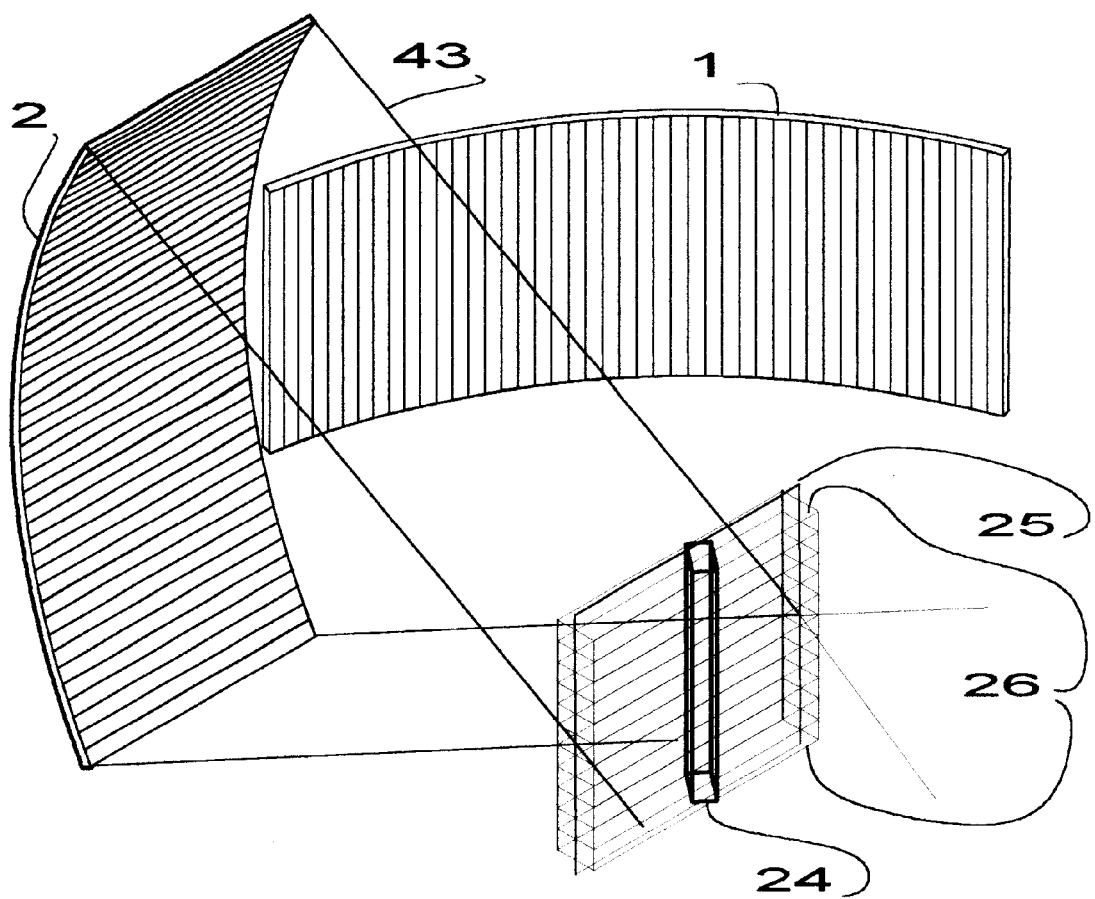

FIG. 5—an orthogonal arrangement of arrays, a transmit beam segment, and a set of receive beam segments.

Figure 6:
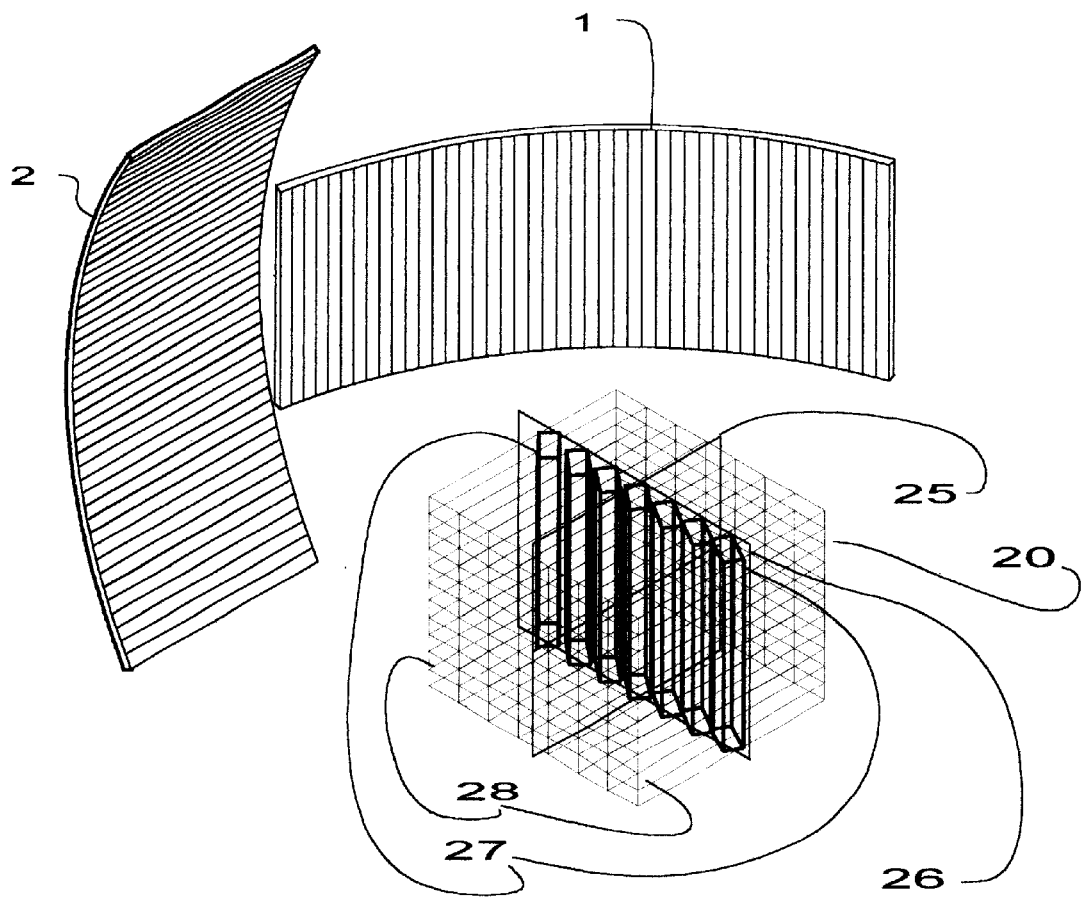

FIG. 6—an orthogonal arrangement in interaction that forms a collimated field of view, with a slice mode arrangement of transmit and receive beam segments.

Figure 7:
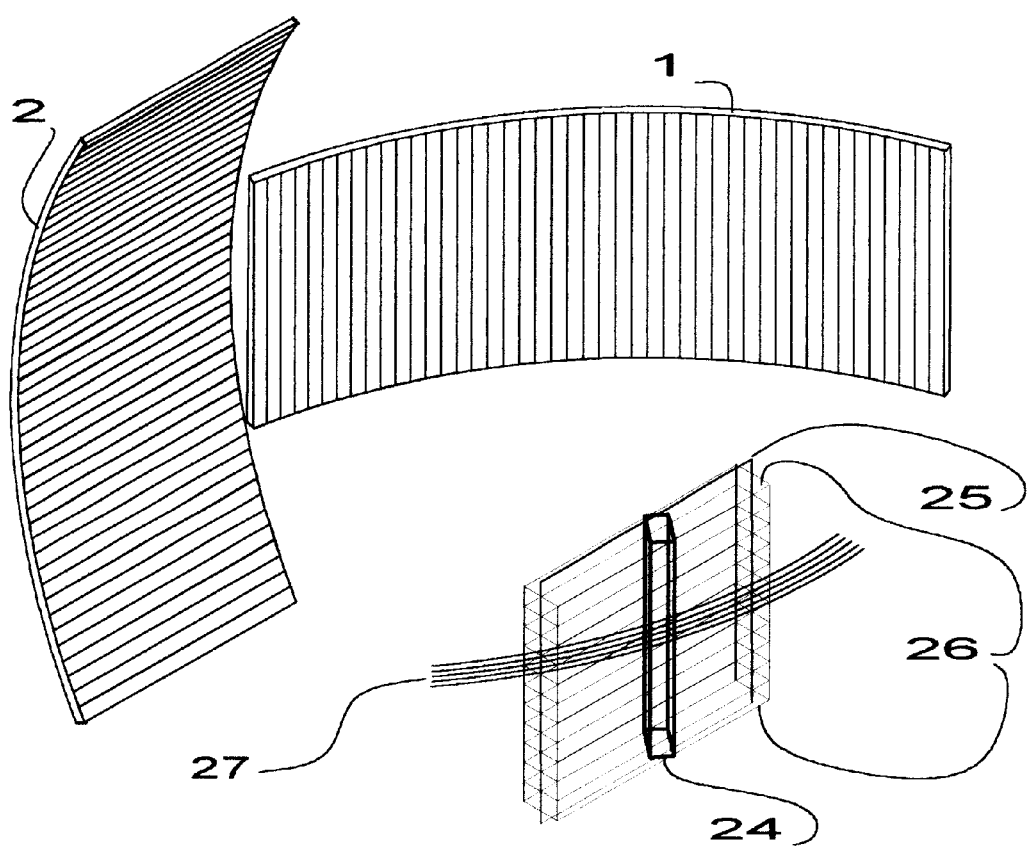

FIG. 7—superposition of fine grain range resolution increments on orthogonal beam segments.

Figure 8:
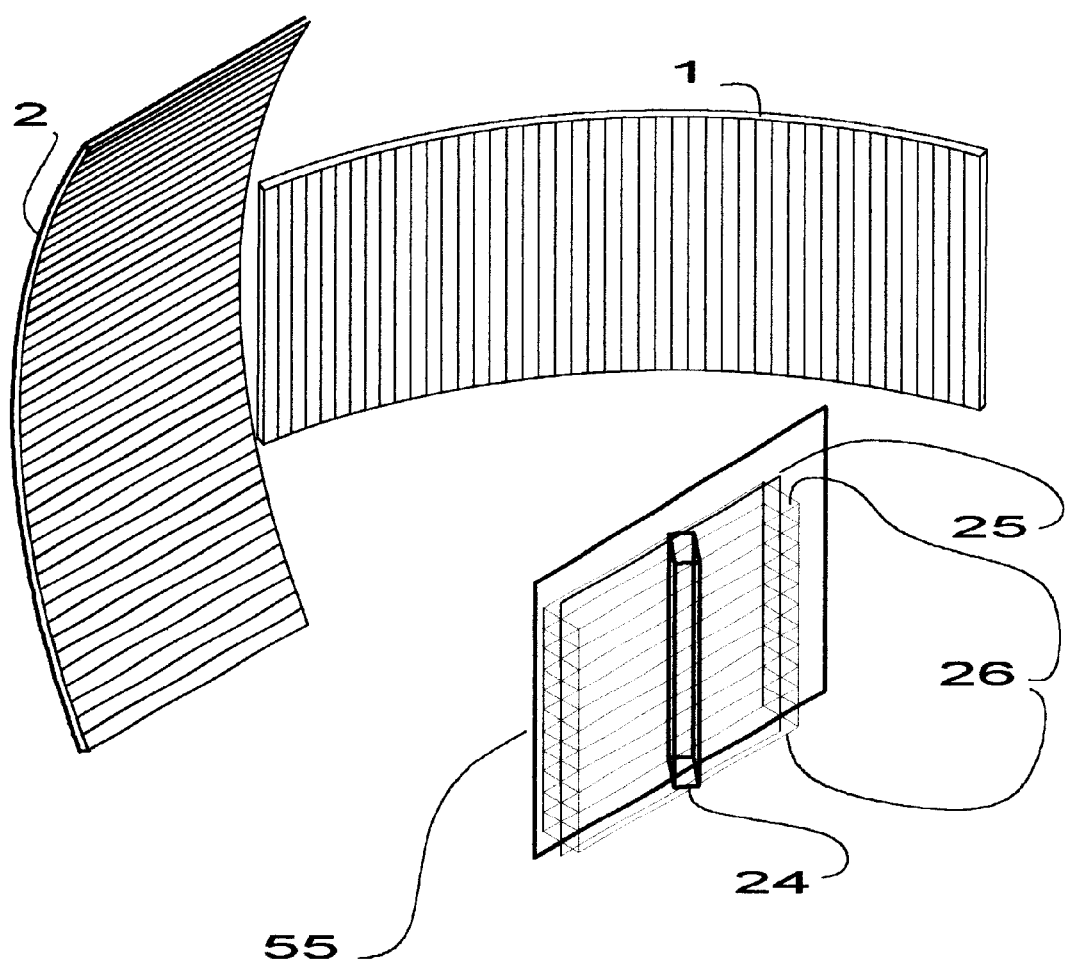

FIG. 8—a planar diffraction control window inserted in radiating signal paths for shallow penetration operations.

Figure 9:
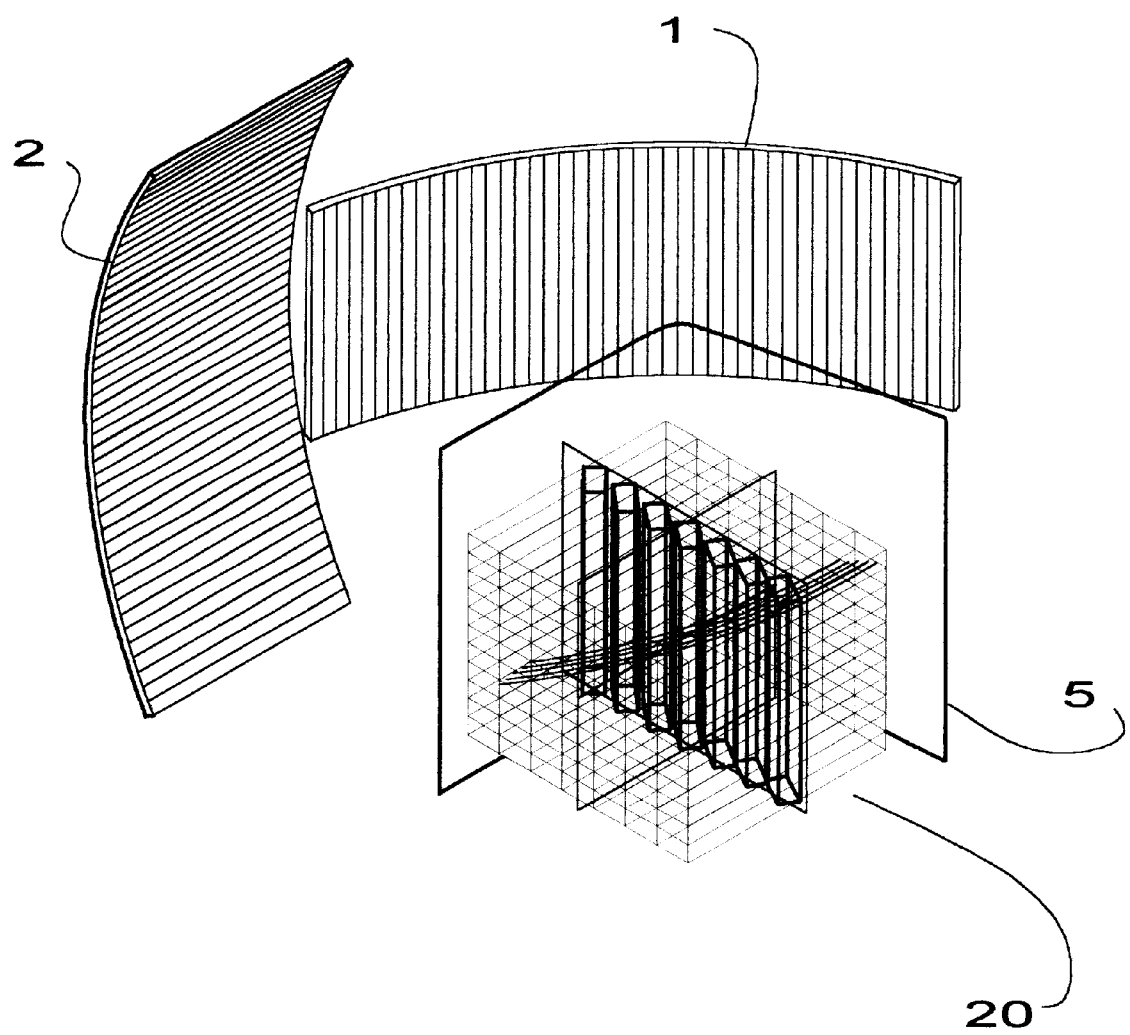

FIG. 9—a shaped diffraction control window for deep penetration operations.

Figure 10:
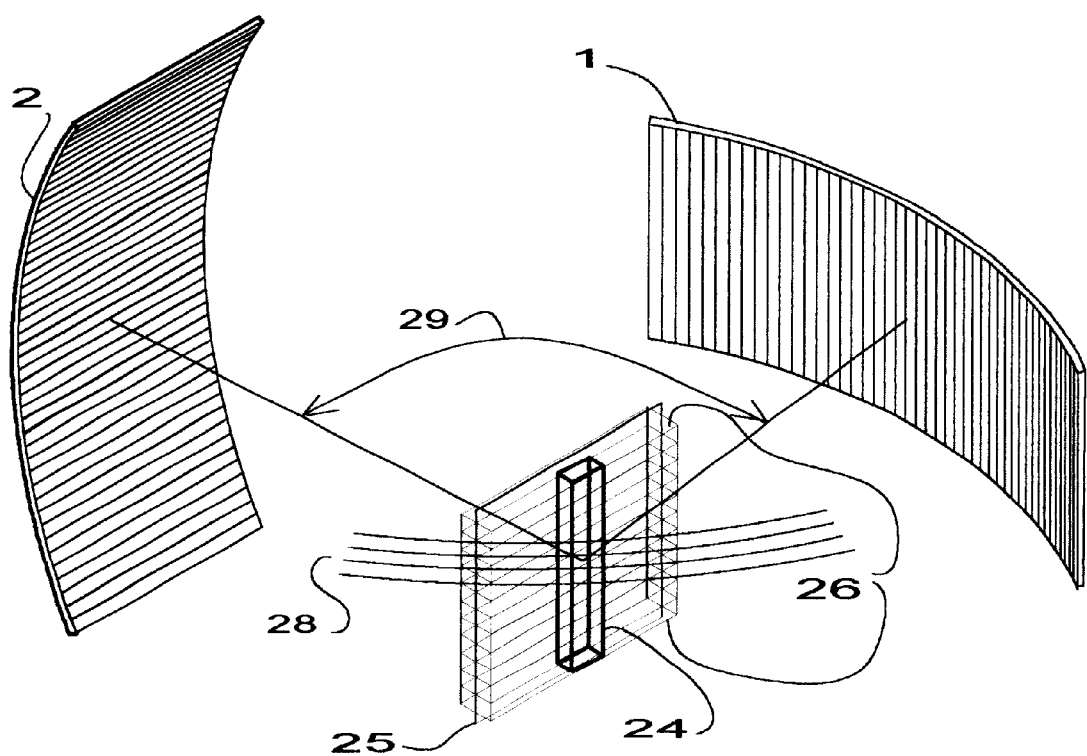

FIG. 10—a bi-static arrangement of arrays optimized for sidelobe suppression.

Figure 11:
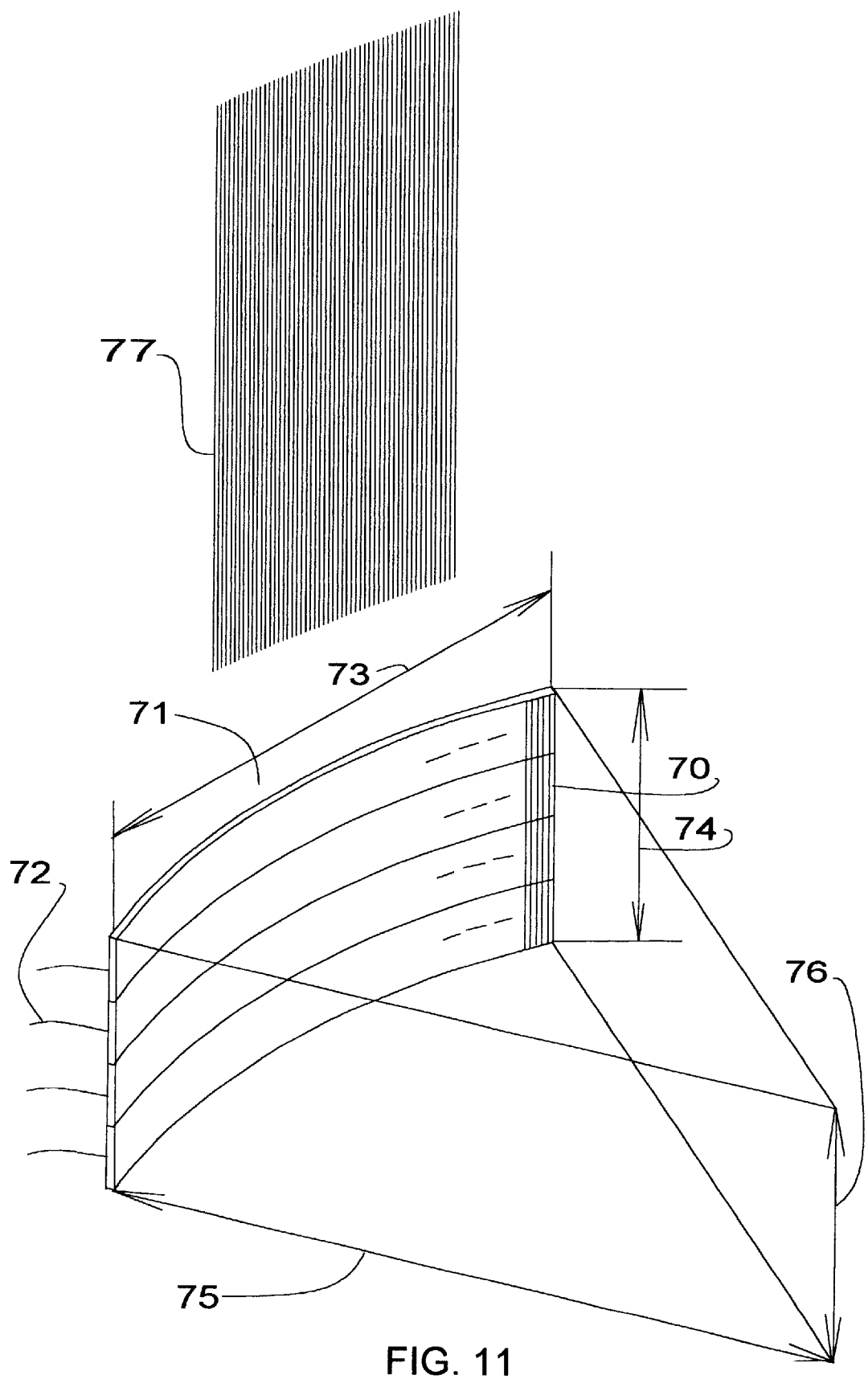

FIG. 11—construction details of a 256 element array with sub-divided elements.

Figure 12:
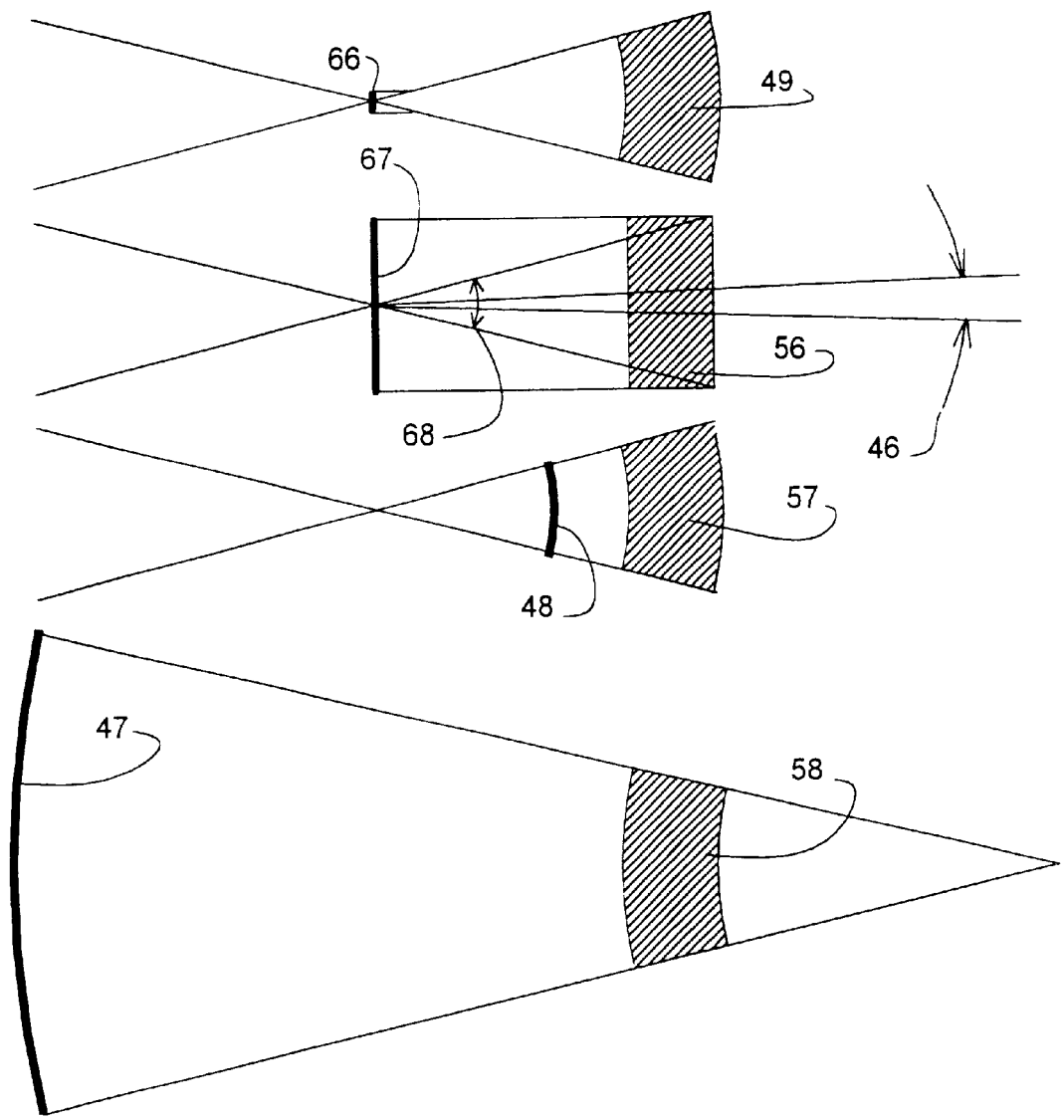

FIG. 12—beam shaping by diffraction compared with beam shaping by geometric effects.

Figure 13:
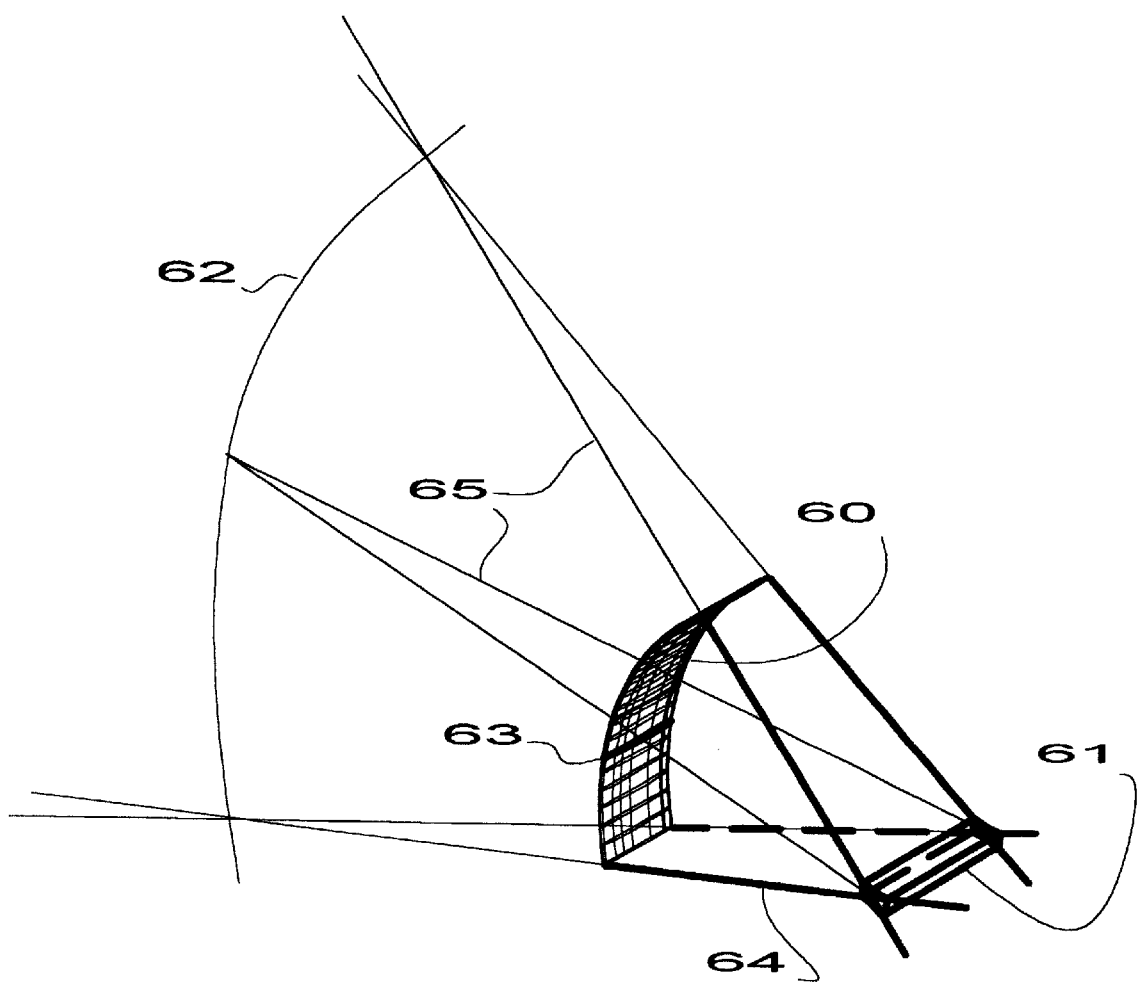

FIG. 13—a convex and concave wavefront with resulting geometric control and diffraction control of a beam segment.

Figure 14:
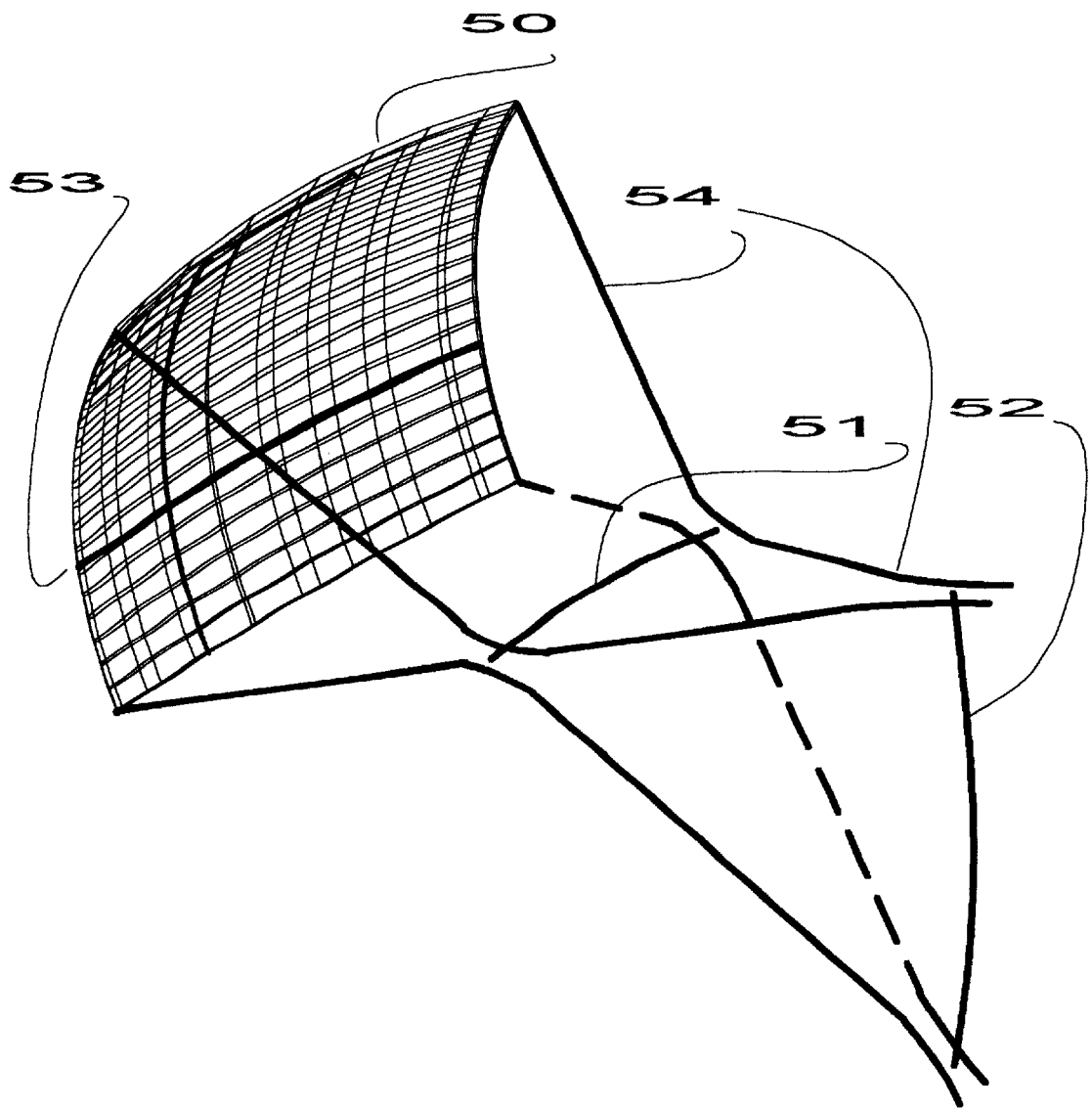

FIG. 14—a concave wavefront with resulting geometric control and diffraction control of a beam segment.

Figure 15:
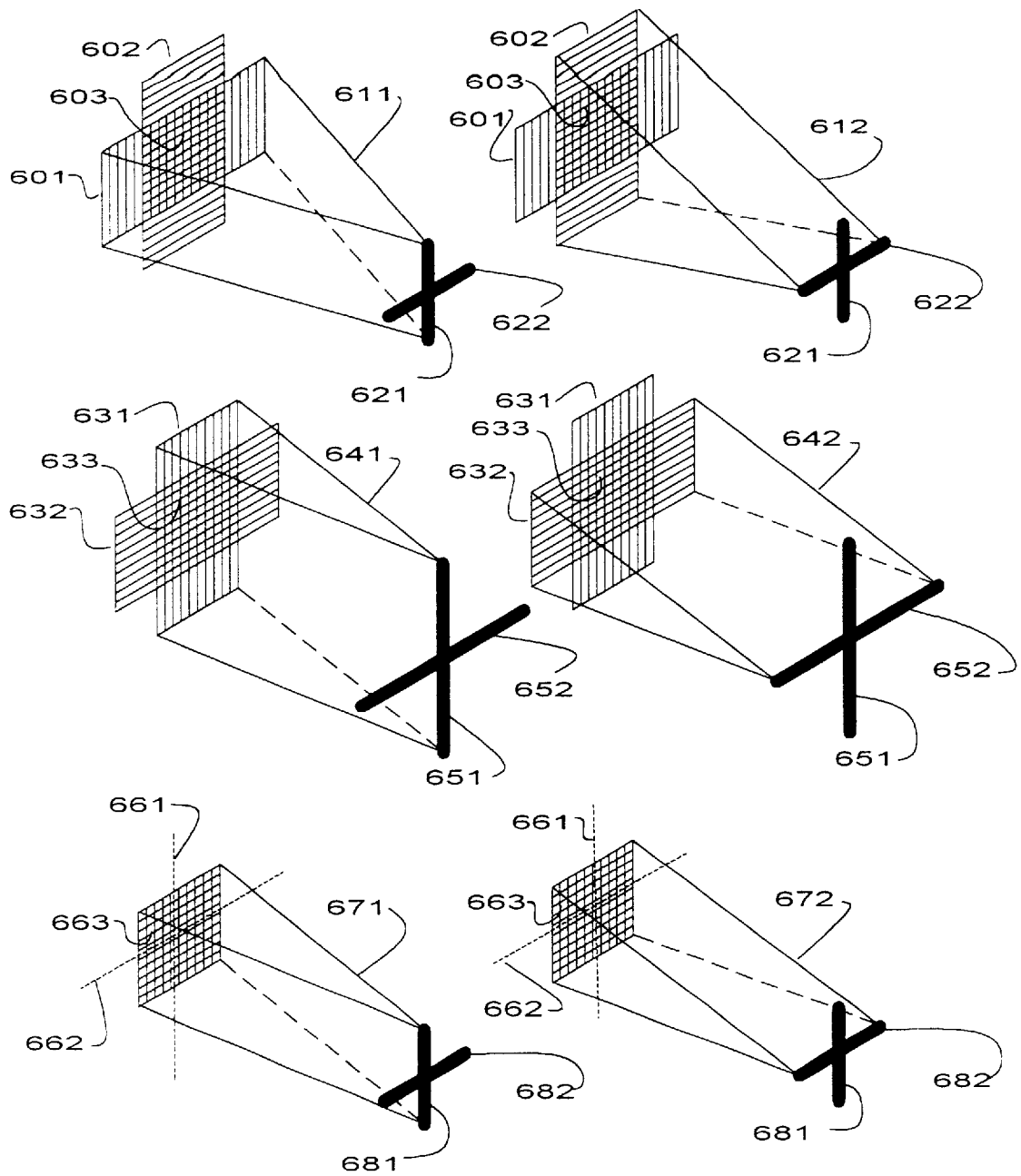

FIG. 15—overlapping array forms with mosaic of interlaced, shared elements.

Figure 16:
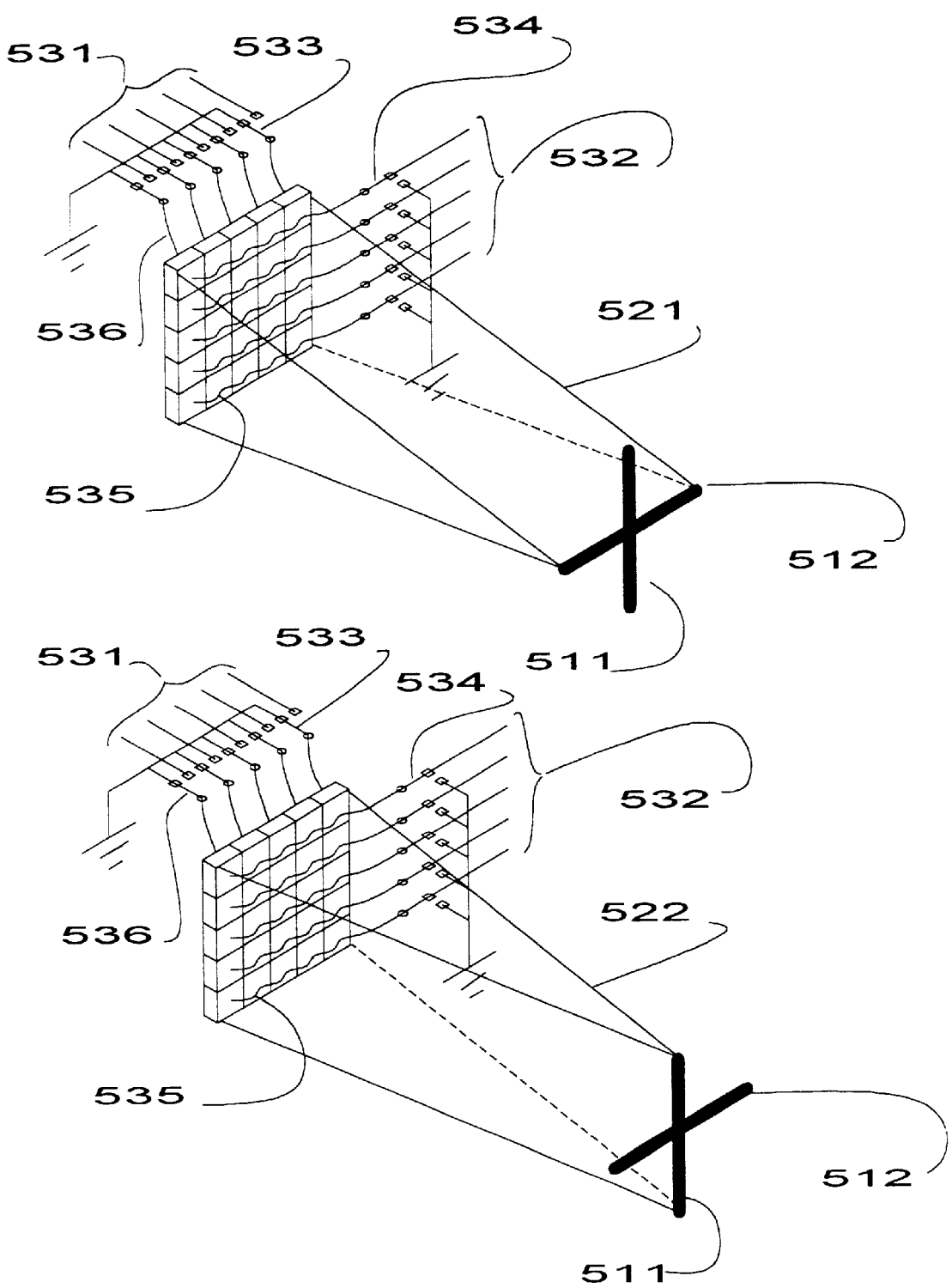

FIG. 16—switching of electrical connections to alternate use of mosaic elements between transmit and receive functions.

Figure 17:
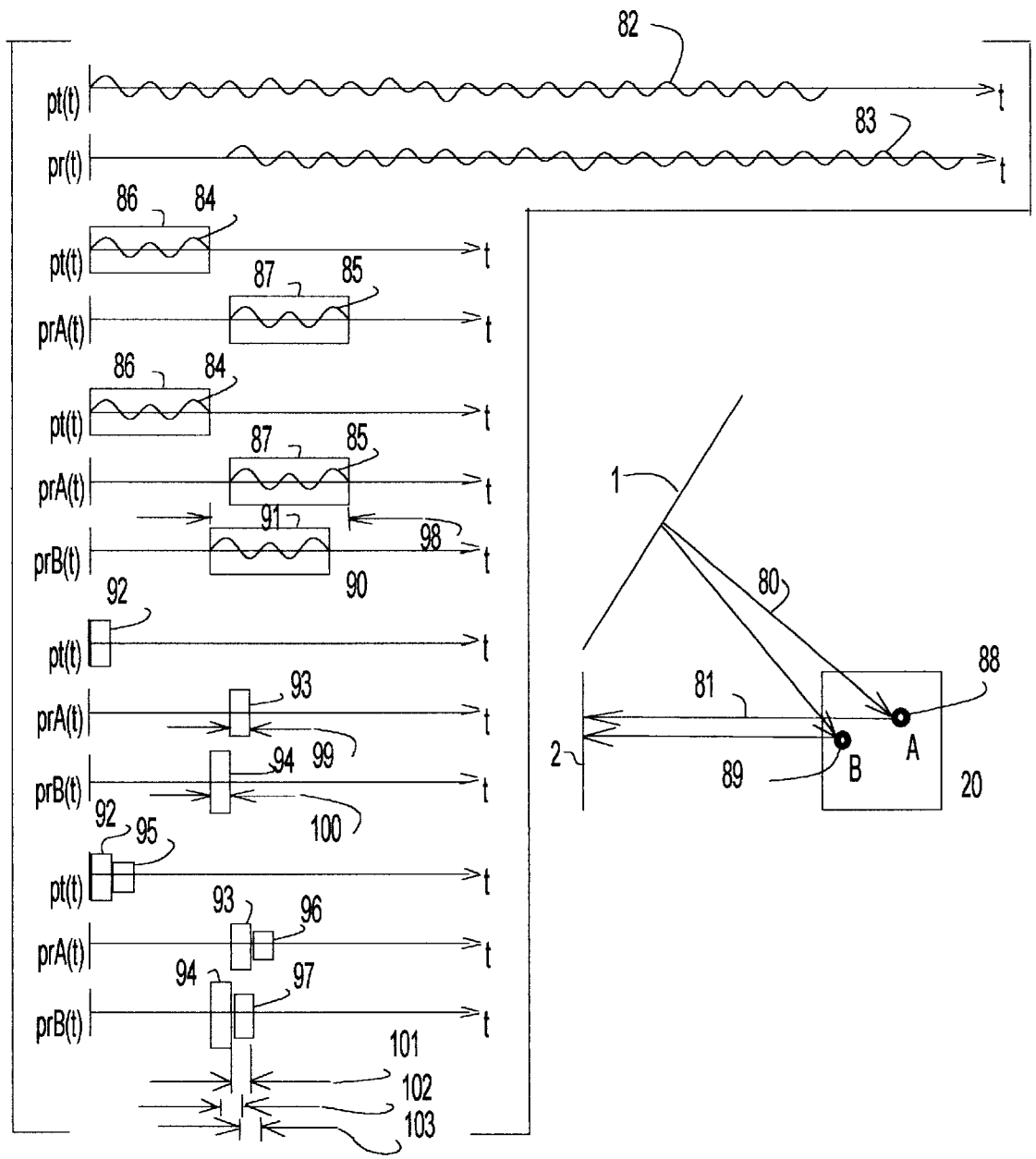

FIG. 17—continuous wave, long tone, short bracket gating, and staggered burst operations.

Figure 18:
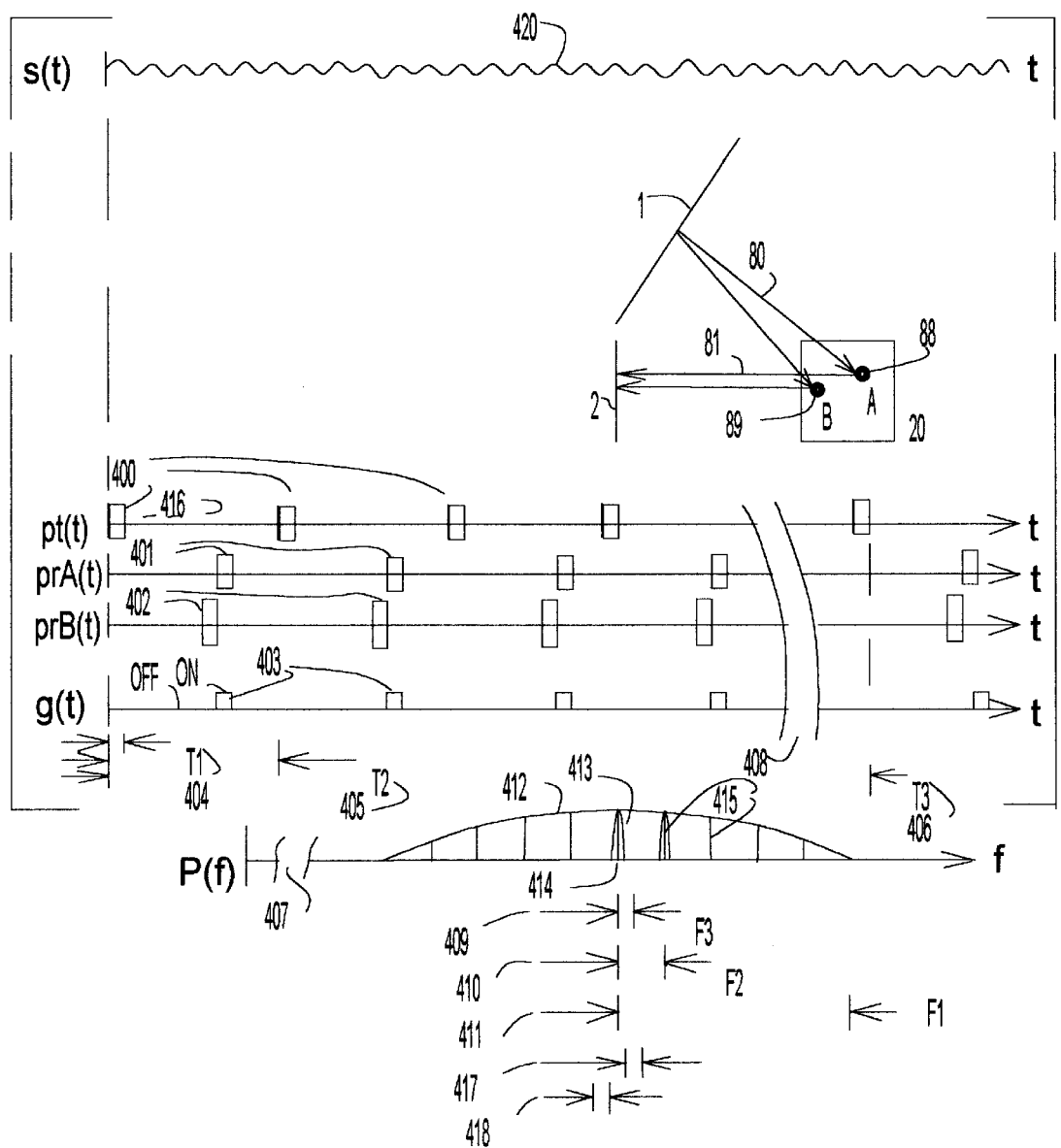

FIG. 18—gated continuous wave operations and frequency domain properties of such waveforms.

Figure 19:
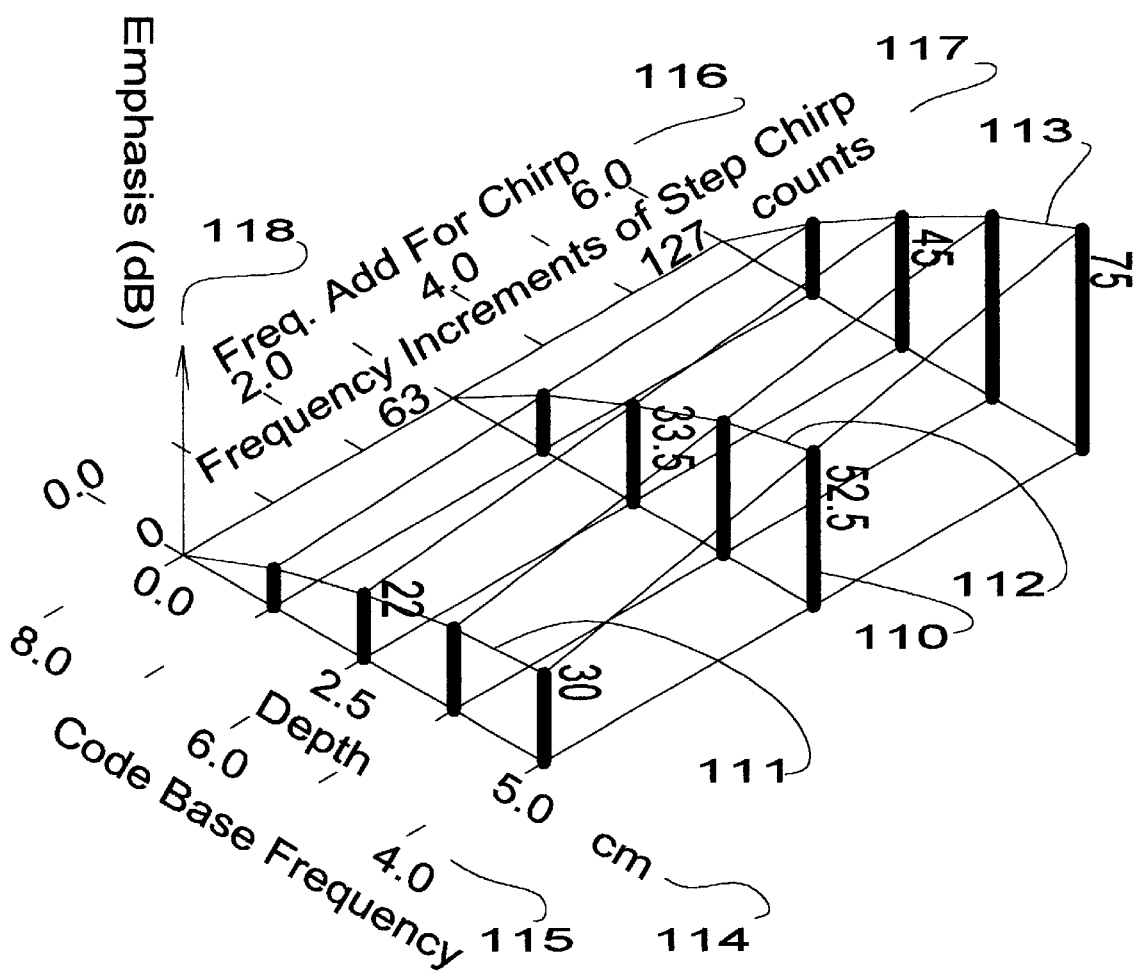

FIG. 19—weighting magnitudes to compensate for varying attenuation for codes and for steps of the step chirp process.

Figure 20:
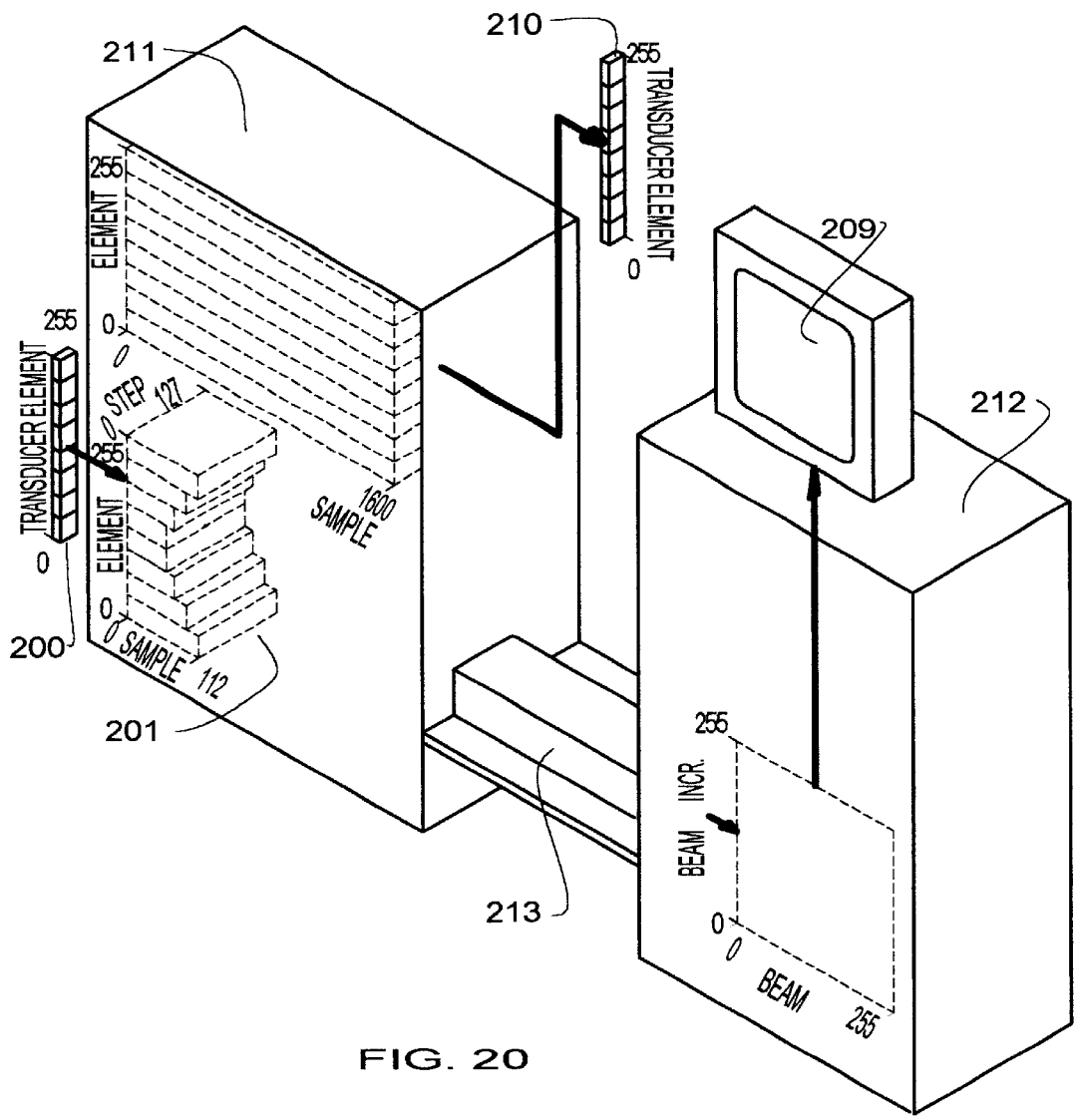

FIG. 20—a general arrangement of arrays, computers, and a display device, with a cut away of one side of the computers to enable viewing of top level signal processing method.

Figure 21:
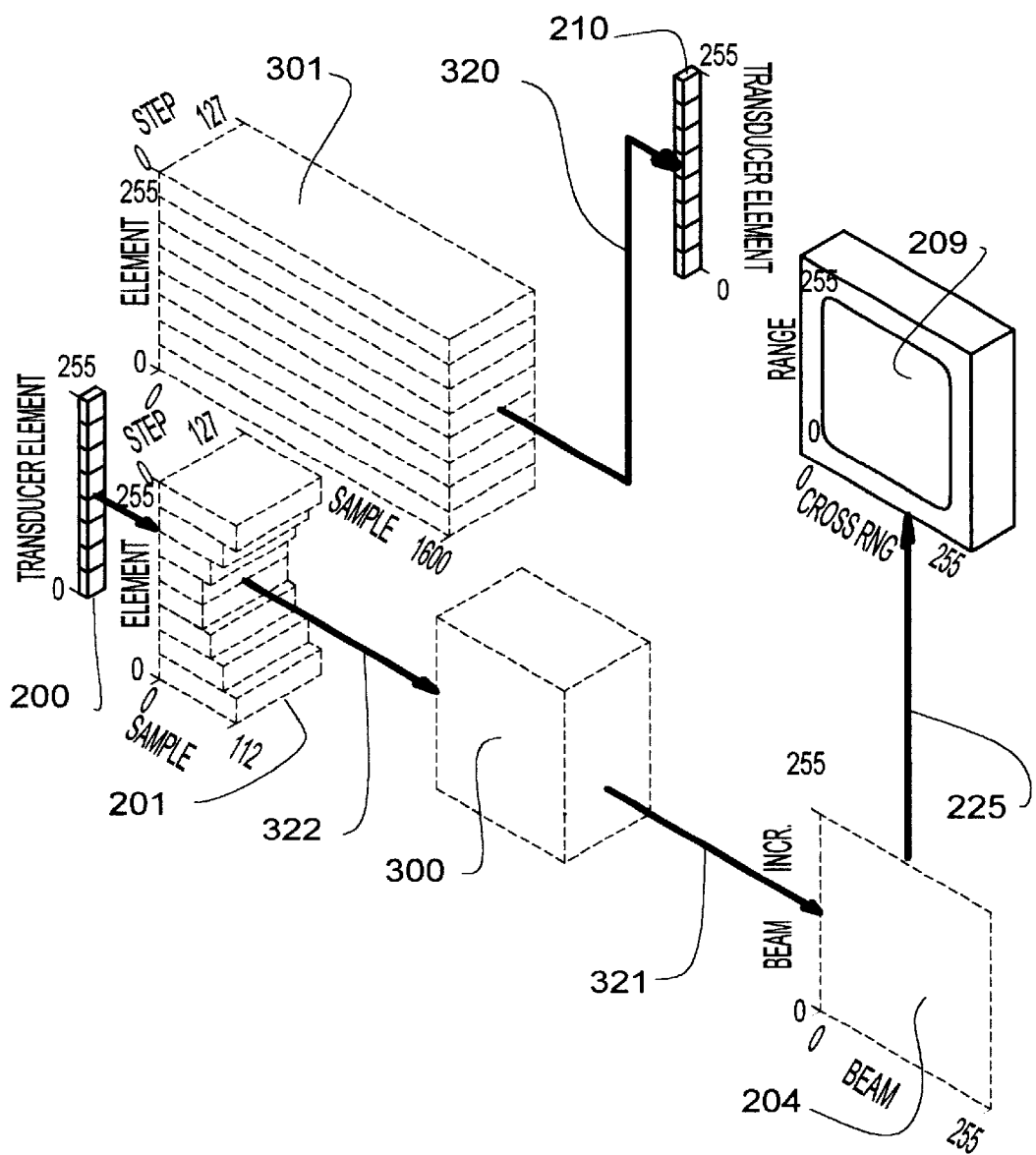

FIG. 21—signal processing operations involving three dimensional matrices and transformations.

Figure 22:
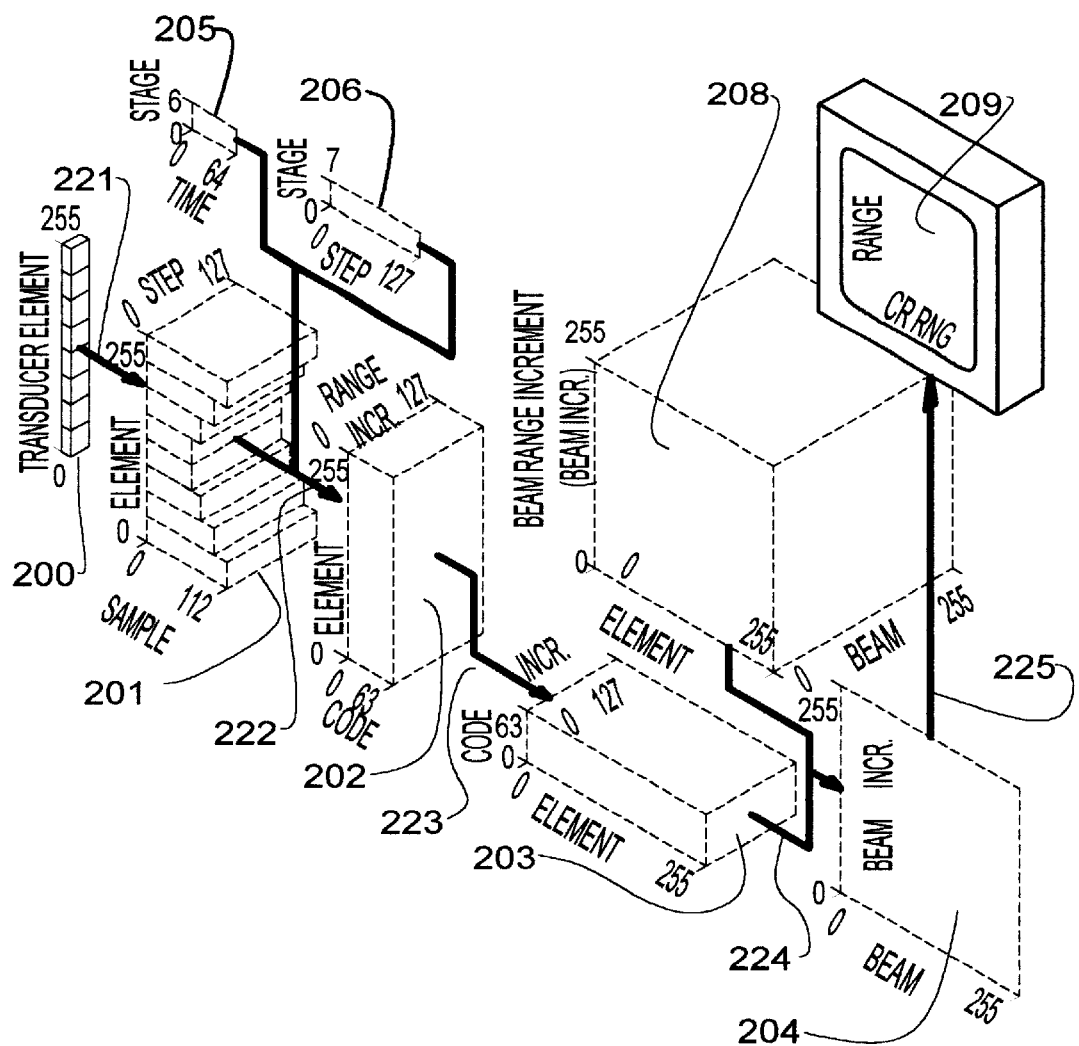

FIG. 22—expanded detail of receive signal processing operations.

Figure 23:
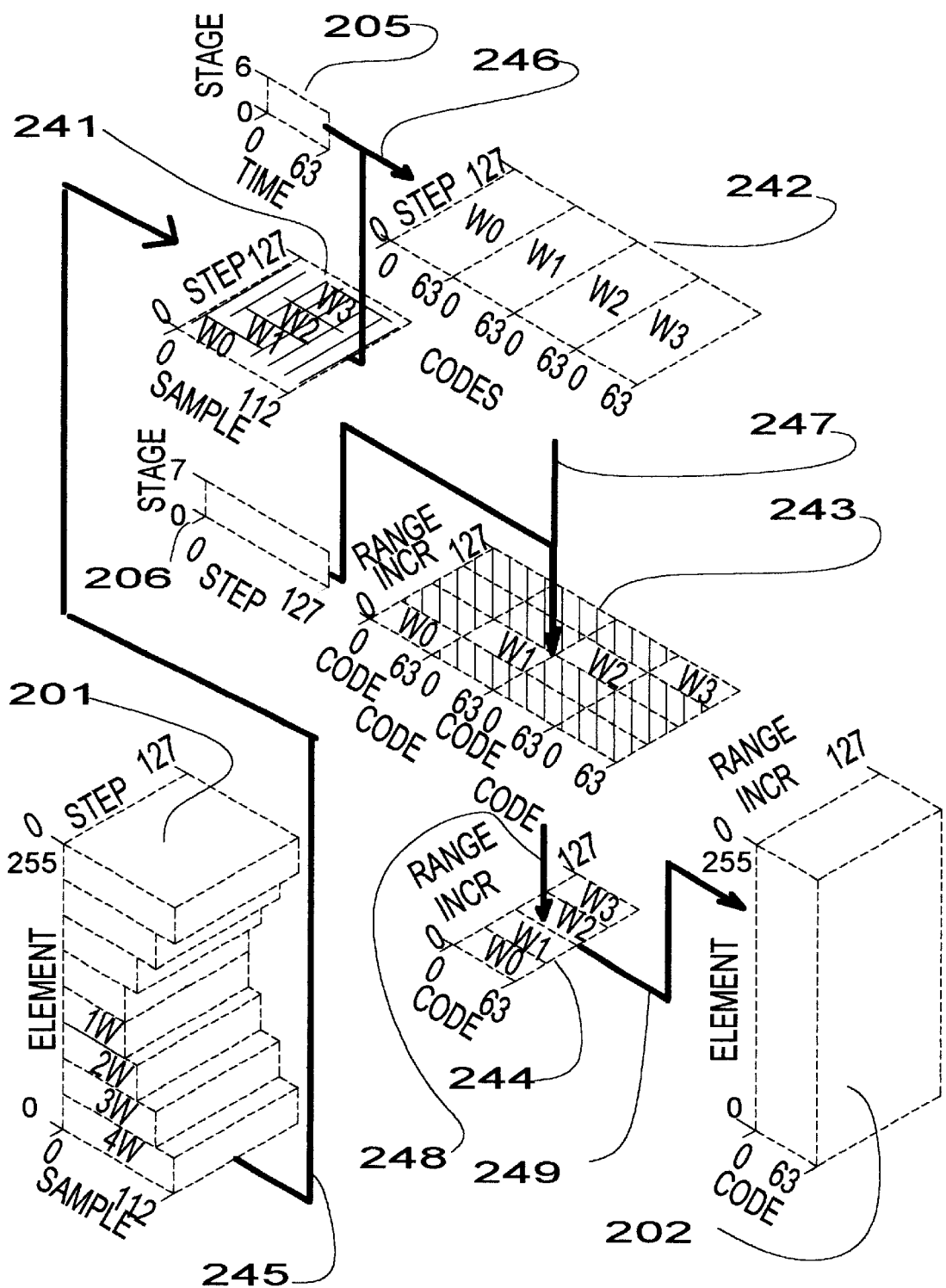

FIG. 23—expanded detail of sliding window processing applied to a sample sequence from a single receive element to extract optimum range increment informtion.

Figure 24:
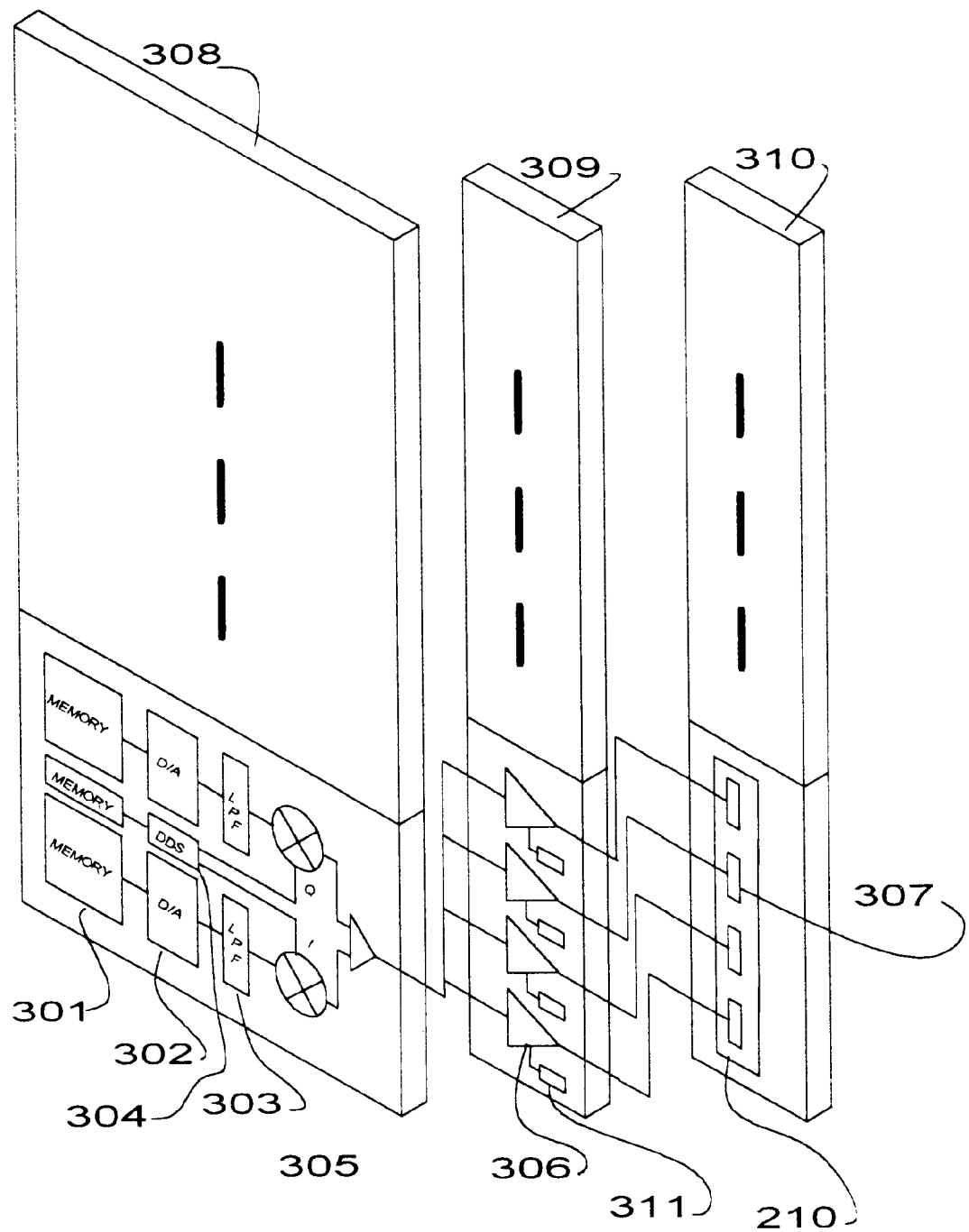

FIG. 24—transmit signal hardware.

Figure 25:
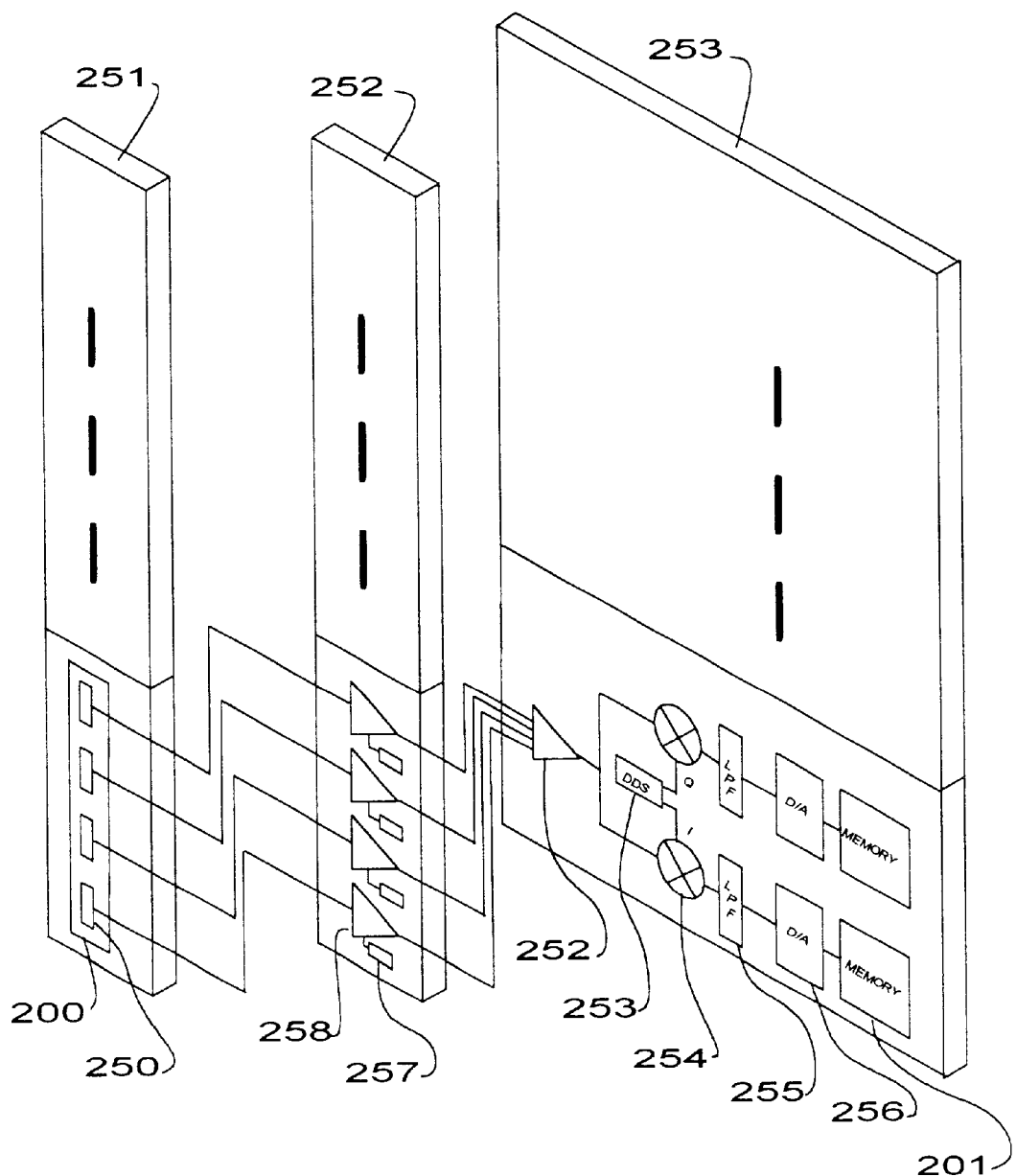

FIG. 25—receive signal hardware.

The preferred embodiment shown in FIG. 1 is a comprehensive medical system for detecting, tracking, diagnosing, treating, and monitoring of healing. The apparatus is a flexible arrangement of transducer arrays and ultrasonic equipment, electronic signal processing equipment, and medical instruments. Provisions are made for an operator to select and plug in a variety of equipment options, to vary arrangement of equipment, and to tune arrangements to optimize performance as on-line adjustments. FIG. 1 is a fixed installation for operation in a water bath. FIG. 2 shows a portable transducer device in a container 69 that moves to a desired location on a patient's body. Operating modes are selectable and programmable by computer methods with software that is under menu control. Signal data bases require extensive advance computation and storage such that actual medical applications are efficient, on-line procedures.

Sensing utilizes ultrasonic signals that are transmitted and received with transducer arrays. Signals are generated, processed and transmitted. Signals are received and processed into image signals. Image signals, or image data, is processed to support detailed tissue tracking and comparative sensing, and operator visualization, and guidance of therapeutic procedures. A powerful parallel computer architecture is a special feature that enables the intensive signal processing and image data processing. Computer and display equipment is in proximity to apparatus shown in FIG. 1 or FIG. 2.

The sensing technology is a new kind of ultrasonic imaging that is called orthosound imaging. Orthosound is a new ultrasonic architecture that is based on the orthogonal array architecture of beamformed television and its variations. The patents, U.S. Pat. No. 5,598,206 (January 1997) Bullis and U.S. Pat. No. 5,966,169 (October 1999) Bullis, disclosed earlier forms of this architecture and are incorporated, by reference, in this disclosure. The term orthosound distinguishes this technology from conventional ultrasound technology that is widely used today. Beamformed television is still the heading for the full family of orthogonal array systems which also include radar wave signal systems. Such general applications are obvious extensions of this disclosure.

The orthosound concept is a central part of the general system. It corresponds to the eyes and brain power of a human being. And as in the human body, where the functions of the eye and brain are important in context of dynamic activity of the human body, orthosound is important in context of the sensing and remedial action sequence of a useful medical system.

The comprehensive medical system of FIG. 1 is oriented to the task of breast cancer control. The pictured apparatus is in a container of water that is open at the top. The container is not shown so as to allow the functional apparatus to be seen clearly. The examination subject leans over the container so as to immerse a breast in the water. Transducers are in a transmit array 1 and a receive array 2 with respective cases 11,12. A refraction control panel 5 controls shape of the interface between skin and water. A transducer 3 for difference frequency sensing is also shown. A visual format display 4, is shown in position to guide a biopsy probe 6, and a precise injection needle 7 with respective mechanisms represented by arms 33, 32 that swivel about an axis 30. The receive array 2 is shown on an arm 31 with capability to swivel about the axis 30. Mechanisms shown are representative of more complex mechanisms that allow translation and rotation of equipment parts to adapt to varying medical needs.

This comprehensive medical system includes plug-in transducer array options that have significant size and shape variations. Many types of transducer systems can be accommodated by the generalized transmit and receive beamforming systems. However, a central theme of the present invention involves orthogonal array arrangements.

Water bath configurations, water stand-off configurations, and direct skin contact configurations are selectable plug-ins. Water may be replaced with a propagation fluid that better matches human tissue, such as castor oil, to minimize refraction. The portable form shown in FIG. 2 contains castor oil with a thin window stretched over the frame 5. The window allows direct coupling of signals from the castor oil fluid and still contains the fluid. An adapter cushion 59 facilitates operation with varying anatomical shapes.

As in previous forms of orthosound, this new system is constructed of a pair of orthogonal arrays located in proximity to each other. Each array is constructed of many transducers. The pair of arrays are arranged for a selected viewing position and orientation. Signal generation and processing is done in nearby equipment that is attached to the arrays by a cable. Images are displayed on a computer screen. Software is utilized to control all aspects of system operation. Operator interface is through a computer system with a menu driven command system.

The orthosound concept is to make images in visual format, like ordinary television images, using wave signals and transducers. Transducers send and receive such wave signals. Transducers are in arrays and the arrays define a radiating surface. The radiating surface is sometimes called an aperture, as if it were an opening of that shape in a screen. If the aperture is not small compared to a wavelength, some directions are more active and it becomes useful to speak of beams that radiate from the aperture. Beams are the primary active signal regions. The central line of such a region is an axis. The beam width establishes cross range resolution for that beam. Cross range can be in units of distance or angle. Most system analysis is oriented toward long range operations so angular terminology is more commonly used. Near field conditions are less awkwardly described in cross range dimension, but the equivalence remains.

Functional definitions are needed for clear discussion of the system. These are related to a simple flat, rectangular, aperture and far field conditions.

An aperture extent determines a resolution angle that translates into the smallest meaningful pixel size that is displayed. This resolution is a primary criterion for comparing imaging or sensing systems. It quantifies capability of a system to distinguish between two objects. A pixel represents a voxel in three dimensional imaging space. Visual format imaging is important for showing a three dimensional volume made up of voxels on a two dimensional display form. Image signal processing includes means to flatten that volume in such a way that human vision can perceive important conditions.

A rectangular aperture has a length, a width and an axis that is perpendicular to the radiating or receiving aperture. A length plane contains the axis and a length dimension line. A width plane contains the axis and a width dimension line. The best resolution is near the axis. Resolution angle, in radians, is the ratio of wavelength to length and the ratio of wavelength to width for resolution in the respective length plane and width plane. Based on radar terminology, it is common for the length dimension to be horizontal and the width dimension to be vertical so that elevation angle resolution is associated with the aperture width and the azimuth angle resolution is associated the aperture length. The resolution is determined by diffraction effects and is called, diffraction limited. It is the minimum divergence angle that can be obtained with an aperture at a particular frequency. This attempts to state Rayleigh's criterion for resolution as applied to rectangular apertures and far field conditions. For operation close to the aperture this rule is inexact, but the approximation is still useful for describing system effects.

The transition from near field to far field in the length plane is where the range equals the length squared, divided by wavelength. Similarly, for the width plane the transition is where range equals width squared, divided by wavelength. A beam from the rectangular aperture is shaped like the aperture in the near field and is said to be collimated. However, for a rectangular aperture the length and width of the aperture differ so the beam transitions to a far field beam at different ranges for the different planes.

FIG. 12 illustrates beam formation in a width plane. The first case is for a radiating surface 66 width that is a few wavelengths. This small aperture 66 forms a fan shaped beam with a field of view 55. This illustrates the minimum divergence that can be achieved with this width for the particular wavelength of the example.

A more generalized concept for near field effects is geometric beam control. Geometric beam control is enabled where the wavelength is much smaller than the aperture dimension. As long as this condition is true, beam shapes are independent of wavelength. Three forms of geometric beam control are shown in FIG. 12.

The first type of geometric beam control is a typical collimated case. This involves a very wide aperture 67 that extends the collimated region to form a rectangular field of view 56 in the illustrated plane. The diffraction limited, minimum divergence angle 68 is shown for the same wavelength that would have produced the divergence angle for the diffraction limited case forming field of view 55. For the very large aperture 67, divergence produces a much smaller cross range extent than the collimated cross range extent. In general, with geometric beam control, the intent is to not form the minimum possible divergence beam.

Two other types of geometric beam control can be thought of as modified collimated forms because the beam control has similar properties. These are also shown in FIG. 12. These types involve radiating surfaces 60, 50 that are circular arcs. These radiating devices are capable of forming respective field of view shapes 57, 58 that are comparable in size to the rectangle form 56. These field of view shapes have little relationship to wavelength as long as the, large compared to a wavelength, requirement is met. The large, concave surface is similar to the focusing shape of long arrays and a sharply focused range exists, except the intended purpose of this form is collimated operation that occurs at a range that is decidedly not focused.

A cylindrically collimated condition is where the aperture has curvature like the surface of a cylinder. This can be either the outside surface or the inside surface of a hollow cylinder. For cylindrical collimation, the beam projects normal to the radiating surface out to a range where diffraction becomes a significant factor. Cylindrical collimation can be either concave or convex, depending on the shape of the radiating surface.

We use the term semi-collimated for operation in a region where the beam is collimated in one dimension and diffraction limited in the other. FIG. 3 shows a semi-collimated beam generated by a wide array. The illustrated array is the receive array but the beam shaping rules are the same for a transmit array. The beam 22 or, more descriptively, beam segment 22 formed by the array 2 has beam width 41 that is the vertical cross range resolution capability for this array. The active region 43 could also be called a beam, but where this is tightly focused the term beam is usually used for the focused region 42. There is a strong depth of field effect for this short range condition. The focused region is arbitrarily defined, at the—3 dB level, as the region until the beam width equals about 1.4 times the narrowest width 41 that is the diffraction limited condition for this configuration. This depth of field effect is one of several range resolving features in the system. The array width 15 is the same as the transverse length of the beam segment 22. Note that this beam segment is decidedly not focused in this transverse direction. The depth dimension 16 of the array 2 has little to do with the beamformed geometric effects, as long as signal timing to the elements is correctly controlled. The array could be flat.

The illustration of FIG. 3 is contrary to the common terms of conventional ultrasound where the beamforming length is arranged horizontally in that system of thinking. The elevation angle in FIG. 3 would relate more to the azimuth angle in terminology of that community.

The three dimensional, semi-collimated effects for the cylindrical collimation forms are shown in FIG. 13 and FIG. 14. These illustrations show wavefronts that are produced by radiating apertures of the same shape, or a combination of radiating aperture and signal timing to produce the equivalent wavefront. A wavefront is a continuous surface over which signals have the same phase. These forms are complicated by the double curvature situation. For the examples of FIG. 13 and FIG. 14, respective axes 62, 52 establish the local radius of curvature for one dimension of the wavefronts shown. In each case the opposite radius of curvature is about the beam segment axis 61, 51. The beam focusing effects are determined by the wavelength divide by the aperture extent in the vertical dimension and these effects determine the beam segment 61, 51 focusing qualities. The collimated dimension is controlled by the boundaries 64, 54 that are geometrically established. For purposes of this disclosure and attached claims, the term collimated or collimation applies to the various types of collimated or collimation arrangements, and collimated systems may be rectangular, concave cylindrical, or convex cylindrical forms.

To explain beamformed television, one can consider first an obvious system that can be constructed with a two dimensional rectangular array of transducers as previously discussed. This can be a visual format imaging system where beams are formed with such an array for either transmitting or receiving or both. For high resolution imaging, such systems are rare since it requires large numbers of transducers to satisfy the conventional rule of half wavelength spacing of elements. Thinning methods are known, but these usually raise sidelobes or cause grating lobes to grow, especially if thinning is carried to out to a significant degree.

Medical imaging involves operation in severe clutter, where clutter is an effect of reflected signals from outside the intended resolution voxel that leak into that intended voxel channel. These leak through the effect of grating lobes and sidelobes and these grating lobes and sidelobes apply to angular dimensions or cross range dimensions as well as range dimensions. Objects outside an intended field of view can leak into an image via grating lobes and result in replication of the object shape in the wrong place. Grating lobe effects are, typically, minimized by very close spacing of transducer elements. Conventional approaches include use of a single array of closely spaced transducers where this array is used for transmitting and receiving. Such systems are well behaved in azimuth but elevation angle effects are poorly controlled. Two dimensional arrays that control the elevation angle as well as the azimuth angle require large numbers of transducer elements and signal processing channels.

Orthosound is a major architectural change that reverses this situation. The concept is profoundly different even though it utilizes much of the experience and technology of conventional ultrasound. It solves the resolution flaw of small vertical line array aperture as would a two dimensional array system, but it generates the aperture effect of a two dimensional array without an excessive number of transducer elements and signal channels. Instead of using a single two dimensional array to resolve two cross range dimensions of a scene, the orthosound method utilizes two arrays that jointly resolve the scene. This is accomplished with two orthogonal linear arrays are used, where one array transmits and one array receives. These are here called a transmit array and a receive array. In simple implementations, transducers in an array are arranged along a line so the length of these linear arrays is much greater than the width, but the deep penetration advantages improve as array width becomes comparable to array length.

Even with this economy in the number of elements, it is still a significant amount of hardware since a large aperture is desired. The usual array methods would dictate that elements were spaced at about a half wavelength so as to prevent the grating lobe problem. When all possible beams are processed, this gives a field of view that is extremely wide. It is much wider than the natural field of view of the human eye. A preferred configuration would involve a large aperture with elements that were spaced to give a restricted field of view. This has severe grating lobe effects.

Solution of the ambiguity problem, or grating lobe problem, is accomplished in the beamformed television method by utilizing the width dimension of the linear arrays. Without increasing the number of channels, the linear arrays use multiple elements in the width dimension, all wired in parallel. These multiple elements form a transverse, sub-array that suppresses response at grating lobe angles of the opposite array. It is reasonable to violate the conventional half wavelength spacing rule along the length of an array because of this suppression effect by an opposite array.

A variation is to simply lengthen the elements, element length being the same as array width. This would use the directional properties of that greater length to similarly suppress grating lobes from the opposite array. The longer element operates much the same as the transverse sub-array discussed above. Arrays can still be described as long, thin arrays. Either the transverse sub-array or the lengthened element method forms diffraction limited beams that can be described as fan beams. They can also be described as minimum dispersion beams. Further lengthening of elements was not excluded in this approach but unexpected benefits arise from extreme element lengthening that corresponds to extremely wide linear arrays. The term linear array becomes inappropriate where the array appears to be more of a flat panel.

The collimated features of the present invention resulted from finding a practical way to greatly extend the elements in the width dimension of the array. Elements became long thin strips crosswise of the array length. The element length dimension is much greater than a wavelength so a collimated condition is established in one dimension only. This semi-collimated condition extends through the field of view so it serves to establish boundaries of the field of view. FIG. 2 shows a single, semi-collimated beam as formed by a wide curved array. In the general concept of beamformed television, beams are wide angle in one dimension and narrow angle in the other dimension. More precisely for the present invention, beams are wide in one transverse dimension and narrow in the other transverse dimension. Transverse is perpendicular to the signal wave propagation direction, approximately. In the field of view the beams are flat and rectangular in shape rather than flat and flaring.

The dimension that is not collimated is the beamformed focus that is a very small, cross range increment. Not only is this a very small increment, the range extent over which narrow focus effects are sharp is limited. This provides a secondary level of range discrimination in system operations.

This semi-collimated method preserves most of the economies of a thin linear array configuration. However, it enables sufficient radiating area so the power intensity at the array surface can be moderate while still giving the need power intensity at the desired depth. This power handling advantage overcomes an undesirable aspect of a thin linear array.

The sequence of FIG. 3, FIG. 4, FIG. 5, and FIG. 6 shows the manner in which a collimated system is developed with orthogonal, semi-collimated beam segments. FIG. 3 shows a receive array 2, a receive element 200, and a single receive beam segment 22. Array length 14, width 15 and depth 16 are defined. A boundary line 43 defines the sensitive region that focuses in one dimension and establishes the collimated effect in the other.

FIG. 4 shows a transmit array 1, a transmit element 100, a single transmit beam segment 24 among a set of coded, simultaneous, semi-collimated, transmit beam segments 27, also generated by a wide curved array 1. A boundary 44 is shown of the active region in relationship to the central transmit beam segment. Transmit array length 17, width 18, and depth 19 are defined in FIG. 4. A transverse plane 25 through the field of view is shown as well. The digital system is capable of arranging such transmit beam segments in arbitrary configurations. The arrangement shown is called a slice mode.

FIG. 5 shows a set of eleven, simultaneous receive, semi-collimated, beam segments 26 overlaid on a single, semi-collimated, transmit beam segment 24. It helps to think of the picture of FIG. 5 as a single system that operates at a single code frequency.

FIG. 6 shows the addition of six more of such systems. The resulting picture involves seven code frequencies. Instead of the one set of receive beam segments 26 intersecting semi-collimated beams and the fully collimated system that results. The slice mode shown is arranged along the longitudinal plane 21. There is now a collection of, sets of, semi-collimated, receive beam segments 28.

A three dimensional block is imaged by this arrangement by repeating the slice mode shown with successive offset planes of slices.

The described system produces a degree of range resolution that is, so far, determined by the focal zone depth effects.

A powerful overlaying system is shown by the addition of a set of range resolution increments in FIG. 7. A set of arcs 27 depicts surfaces that are range resolving boundaries that are provided by the step chirp process. Here is shown a single code frequency and a single set of simultaneous receive beam segments, as in FIG. 5. This makes it possible to see how the range resolving surfaces become the primary determination of the range resolution cell in a particular intersection of a transmit beam segment and a receive beam segment. The other range resolving effects become secondary, but this secondary effect is important in controlling sidelobe and grating lobe leakage from most of the volume wherein signals radiate.

It is important to note that sidelobes of a beam range increment are of concern if they are within that beam range increment. The fact that range increments are at an angle to the focal zone means that much of the sidelobe energy will be de-focused because arcs 27 do not stay within a particular receive beam segment for a very large angle extent and sidelobe energy from the larger angles is cut off by the range resolving boundaries. This is due to the angular difference between excitation signal angle and reflection signal angle as well as the curvature versus the straight form of the beam segment. This can be optimized somewhat by an operator with the capacity to adjust the bistatic angle to make this effect more pronounced. The bistatic angle is the angle between the two arrays. FIG. 10 defines the bistatic angle 29. In the configuration shown the angular difference is in only one dimension, but flexible positioning capability, that allows raising and lowering of the transmit array 1, enables optimizing this effect in the other dimension as well.

Visualizing the full set of system functions requires both FIG. 6 and FIG. 7 in overlaid arrangement. The beam segment shapes shown are representative of an actual system where there are 256 elements in each array to form a cross range resolution grid of 256 by 256 beam segments. A step chirp resolution matches the cross range resolution to give a full three dimensional block of about two million voxels.

There are multiple resolving mechanisms involved. At this point, the transmit beam segment width and focal zone depth, the receive beam width and focal zone depth, and the range resolving capabilities of the step chirp have been mentioned. Bracket gating is a further resolving mechanism that adds to the resolving power of the system. Attenuation compensation, element sub-dividing, and refraction control are special parts of the deep penetration orthosound system that refine resolution capabilities. Appodizing, tapering, shading, null steering, adaptive beam shaping, aberration correction are common measures to apply to refine resolution capabilities.

Rectangular field of view imaging is a direct result of the semi-collimated, orthogonal arrangement. A flat focal plane effect also arises from the semicollimated beam system. This simplifies image processing and display in rectangular coordinates. Scan conversion is not needed to correct for curvature. Simplified system programming will provide rapid acquisition of a single cross range image.

One array defines two opposite sides of the field of view and the other array defines another two opposite sides of the field of view. In this way a fully collimated system is created. The range extent, or depth extent, depends on signal operations. As with previous forms of beamformed television, the array length still is used to give high resolution of the transverse dimension of the field of view.

Refraction occurs at the boundary between propagation mediums that have different velocity properties. For a water bath, the transition to human tissue results in refraction that tends to de-focus beams. FIG. 8 shows the addition of a planar refraction control window 55. A thin polyester window material is stretched across the dark frame shown. This window is oriented such that it is parallel to all array elements. This means that corrections in phase can be applied to a full element to compensate for refraction effects at the boundary of water and the patient's body. The width extent of the water tissue interface is not excessive for shallow penetration, but for deeper operations a more involved window is needed. Such a window 5 is shown in FIG. 9. This window also has a tight polyester window and provides the same parallel surface function. The corrections are more involved, but will be constant once they are determined. Mylar is a trade name polyester material that is known for strength so a thin sheet can be used. A thickness less than one quarter wavelength is appropriate.

For either window it is desirable that good contact be made. In a water bath situation, this can be enhanced by pressing the skin against the frame and pumping the residual water from between the skin and the window material. This is made effective by a frame thickness that allows water to be pumped out from around the edges of the frame. A vacuum bag effect will then be realized. One type of window is attached to the patient. For fluids that are disagreeable to a patient, the window serves to prevent direct contact with the skin.

The element length dimension, which is the array width dimension, is further subdivided for deep penetration effectiveness. Greater depth results from greater signal strength that results from better impedance match with the drive amplifiers. By separating elements into sub-elements that are individually wired to respective power drive amplifiers and to receive pre-amplifiers, a transformer like effect is achieved. This sub-division is separate from sub-divisions that improve surface displacement response of the piezoelectric material. Uniform drive, or gain, over the full length of the whole element is needed to get the collimation effect. FIG. 11 shows a full wide array with sub-divided elements. An expanded view of a surface 77 shows the shape of an element in a 256 element array. The desirability of subdivision into four pieces is seen in perspective in this view.

The smaller sections of transducer material significantly reduce the risk of fracture from handling.

Because the sub-elements are individually connected to amplifiers, both for transmit and receive, it became possible to implement switching capability that selects any array quarter. This means that the field of view can be immediately restricted to one eighth of normal. Other sub-dividing combinations are obvious. This gives a powerful diagnostic mode that has significantly reduced sidelobe effects compared to the full field of view system. This is especially useful for sensing regions of very low signal level return. The switching is accomplished by biasing transistors to the off state. This is done at several stages of the amplifiers to prevent leakage effects from occurring.

Slice mode is a two dimensional mode that does not require a block field of view. Hence, it is desirable for the field of view to be reduced as far as possible in one dimension. Turning off sections of the receive array accomplishes this. Where three dimensional operation is accomplished by successive slice mode operations, the receive array sections are sequentially switched to accommodate the moving slice. This means that clutter sources are reduced in number to one fourth of the number for a full field of view. This can be thought of as a sub field of view. An important design implication is that this reduces the dynamic range requirement for the analog to digital converter.

Refraction control was discussed for wide elements where a special parallelism was required. For reduced width elements, the corrections are more effective in situations where parallelism is inexact. The sub-divided elements enable separation of propagation paths and handling these individually. Thus, complicated path variations can be corrected. For selected portions of the field of view, propagation paths are measured and phase adjustments are calculated and applied.

This semi-collimated method is very beneficial where it is ordinary rectangular collimation. However, other arrays are in the convex cylindrical collimation form in one dimension as a variation that increases the radiating area to a lesser extent while allowing thinner arrays. With convex cylindrical collimation, the edges of the beam are radial lines rather than rectangular. FIG. 13 illustrates a convex, semi-collimated beam 61.

Another array form is the concave cylindrical collimation method. This causes simple focusing in one dimension, but this focusing is not used for resolving purposes since such focusing is beyond the field of view. Instead, the converging beam shape is used to define the field of view. This array form provides the greatest power handling capability. FIG. 14 illustrates a concave, semi-collimated beam segment 51.

For purposes of this disclosure and attached claims, the term collimated applies to the different types of collimation discussed here.

Array system that utilize cylindrical collimation yield significant performance advantages at the penalty of more complex image processing to deal with the curved focal zones.

FIG. 15 shows array forms where the orthogonal arrays overlap. This is possible with very thin arrays, or where one of the arrays is very thin. Otherwise there is a conflict in the overlapped region. This is shown in FIG. 15 as mosaic regions 603, 633, 663. The arrangement of arrays 601, 602 with elements that are shorter than the array length is most comparable to the forms previously discussed. The elements in the center overlap in a mosaic pattern. However, there are situations where arrays 631, 632 are wider than they are long. These also overlap and elements cross in a mosaic pattern 633. Square arrays 661, 662 are also useful for small footprint applications where the viewing window into the body is restricted. Orthogonal beam segments 621, 622; 651, 652; 681, 682 are formed by these array configurations and the combinations all form collimated systems from interaction of semi-collimated beam segments.

FIG. 16 shows the arrangement that enables the active, piezo-electric, in the mosaic region to be configurable into elements of either array. This mosaic region thus can operate as either transmit elements or receive elements. Transmit lines 531 and receive lines 532 are alternately connected to transmit wires 536 and receive wires 535, respectively. In opposite sequence, transmit wires 536 and receive wires 535 are connected to ground potential. Virtual ground potential is sufficient for transmit wires 536 grounding and a diode path to ground is sufficient for receive wires 535 grounding. The lower illustration shows an arrangement and switch connections for forming a transmit beam segment 511 with an active region 521 defining the field of view height. The upper arrangement is for forming a receive beam segment 512 with an active region 522 defining the field of view width. These operations depend on the switch positions, or equivalent sufficient electrical conditions.

Very small transducer array systems, as above, are fabricated with silicon integrated circuits that include the switches, drive electronics, and receive electronics on two respective silicon chips. These chips are connected to the set of transmit wires 536 and the set of receive wires 535, respectively, and then folded onto the back of the array. This forms a compact package.

For sub-divided elements, the switching shown in FIG. 16 involves multiple parallel switch banks instead of the single switch banks 533, 534 shown.

The previous discussion addressed physical and geometric concepts The remaining discussion addresses signal forms and methods of generating, radiating, receiving, and processing signals.

A basic mode of the present invention is a simple pulse mode that is like the simple pulse mode of conventional medical ultrasound systems, except it is organized to fit the orthogonal array configuration. Because beams are wide in one transverse dimension and narrow in the other, a single broad angle pulse transmission fills a rectangular slice volume, with the slice thickness spreading with depth. Simultaneous receive beams are formed as parallel channels that capture all returns from this transmission and form channels that correspond to respective directions, or cross range displacements. However, because of near field problems, the effective depth of field is very small. This means that multiple pulse transmissions are required, in sequence, to adequately focus throughout this slice. The direction of the transmit beam is moveable so the slice is shifted throughout the three dimensional volume of the full field of view. This allows full three dimensional acquisition, but it requires multiple transmit operations for both the multiple focal zones and for the multiple transmit beam angle, or cross range displacement, positions.

The range resolution is an inherent property of the simple pulse waveform, that is, it is the range equivalent of the pulse time duration. This is an optional mode of operation where attenuation is not extreme. This mode meets the acquisition time requirement for many cases. Simple pulse mode is illustrated in FIG. 17 where a simple pulse 92 is transmitted from an array 1. After reflection from objects A 88 and B 89 the received signals 93, 94 are shown on parallel time lines. This illustration shows the timing separation that would just enable object A and object B to be resolved in range and the inherent property of the simple pulse waveform to resolve in range is thus demonstrated. For simple pulse operations where the only range resolving means was the pulse width, the pulses 92, 93, 94 would be much shorter than this illustration can represent.

Beamformed television provided for coding that would further reduce acquisition time. Such coding included long duration waveforms that could be simultaneously transmitted and radiated so that a code was associated with a respective transmit region. This could be used for simultaneous transmit focusing at multiple depths, or simultaneous transmit beam operation at multiple angles, or a combination of these. A powerful mode, that is an option in the present comprehensive system, is to use codes that are noise like waveforms, such as pseudo-random noise, that can be recognized and sorted with correlation processes after reception. These result in time domain functions that are about the same as simple pulses. These codes are generated in advance of system operations and stored in memory. Transmission is in a burst operation. Received signals are matched with a replica of each code to extract that code. This is a correlation process that can be done with time compression correlation or with an FFT based process. For the FFT method, a multiplication of a set of frequency domain samples and an inverse FFT are required for each code. This is a lengthy signal processing operations so there is penalty in system timeliness for this type of operations. They also are subject to the need for bracket gating, meaning the time duration of the waveforms is limited, since the correlation occurs after sampling by the analog to digital converters.

A coding system that is more efficiently processed is utilized for the primary mode of operations. This system utilizes simple frequency tones as codes. A set of such codes can be recognized and sorted with a single FFT process. FIG. 19 shows a five code arrangement with the spectrum content of a single burst being represented by the scale 115. In this simplified illustration, there are discrete frequency of 8, 7, 6, 5, and 4 MHz transmitted simultaneously. The shape of the spectrum 121 is shown with weighting to be discussed later. For a larger number of codes, the frequency components would still be described by the spectrum shape 121.

The bracket gate evolved from known techniques to deal with the problem of receiving a very low level signal while transmitting. In typical step chirp instruments each tone that is a step is very long such that it is considered to be a frequency domain measurement. Signals transmissions continue through the time of reception and a long term overlap occurs. For linear systems the duration is not a problem, but where analog to digital conversion is involved there are significant limitations. The difference in signal level is often so significant that when gain is reduced to prevent saturation, the sought after signal is so low that the smallest digital bit does not respond to it. This dynamic range problem occurs at the analog to digital converter. If the transmitted tone is terminated before reception, this problem is solved.

In the deep penetration situation, clutter problems become the issue. In deep penetration operation in highly attenuating media there is a much stronger reflection from short range objects. As with receiving while transmitting, this can result in signals from deeper object being overwhelmed by signals from shallower objects. In medical imaging, there are many such scattering source objects. The solution is similar to that used to solve the transmit while receive problem, as discussed above, except the tones are made much shorter so that the field of view is actually resolved to a coarse degree. Now, reflections from deeper objects arrive after reflections from shallower objects. The receiver needs to operate only after the shorter range signals have passed. These tones can be shortened until the widened signal bandwidth exceeds the allowable system bandwidth. The shorter the tone duration, the fewer is the number of codes that can be fit into the system bandwidth. The present invention achieves a satisfactory balance of these requirements.

The evolution of bracket gating is demonstrated in FIG. 17. For long duration codes, the continuous wave condition becomes valid. FIG. 17 depicts a long duration waveform 82. For the signal paths 80, 81 with the associated geometrical arrangement, the reflected signal 83 is shown on a comparative time line 107. In the illustrated case, transmission continues during reception. For low level reflections, a very wide dynamic range receiving system is required to extract received signals from the transmitted signals.

Simple separation in time is accomplished with a waveform 84 of moderate duration 86 such that transmission and reception as seen on a comparative time line 108 do not overlap. The envelope 87 of reflected signal 85 from object A 81,88 and the envelope 91 of reflected signal 104 from object B 106, 89. This pulse or tone is of such long duration that it barely qualifies as a pulse. It still can be processed as if it were a continuous wave signal. The signal reception process is simply not done during transmission but is otherwise continuous.

Although time separation for transmission and reception is accomplished by this arrangement, the comparative time lines 109 of tone arrival times from different objects shows large overlap between reflections from the two objects 88, 89. Time domain efforts will not resolve the position of the two objects because of the large overlap. However, the transmission envelope 86 can contain two tones at the same time that are arranged to focus at different ranges or angles. Then returns from object A 88 are seen as a waveform 85 of one frequency and returns from object B are seen as waveform 104 of another frequency. At the point of reception these reflected signals are on the same electrical wire. A sequence of samples can be arranged that will acquire both signals simultaneously. If the two signals are coded, then a pair of simultaneous filters can be applied to extract the two separate codes. This only provides crude time resolution because the focal zone boundaries are not abrupt, but it does provide well defined directional information. A sharp separation of angles of paths 80, 105 can be accomplished. Long duration tones enables more codes that can be resolved in the frequency domain since the resolvable tone separation, in Hertz, is one divided by the tone time duration, in seconds.

To get sufficient image range resolution using time domain methods, a 0.2 microsecond pulse is required. For 0.2 microsecond pulses, the resolvable tone separation is 5 MHz. For operation centered on 10 MHz, this requires a very large percentage bandwidth system just to transmit that pulse. Even two frequency codes would require more than the available system bandwidth. It is not feasible to code simple pulse systems unless much longer pulses are used. Longer tones enable coding systems, but another method is needed to get fine grain range resolution.

It was found in system design, that using longer tones 84 such as shown in FIG. 17, resulted in a clutter problem since the reflection points, such as objects A and B 88, 89, are extremely dense in human tissue. The act of receiving reflections from an object, at the range of object A 88, was made extremely demanding by the fact that the signal attenuation for the path to 35 and from objects at the depth of object A 88 was much greater than the corresponding path to and from objects at the depth of object B 89. An analog to digital conversion process required that a large number of bits be resolved to avoid saturation for high level signals and still respond to low level signals that were able to influence the least significant bit. This motivated a pulse duration that would exclude paths of low attenuation while trying to receive over paths of high attenuation. A bracket gate arrangement was enabled by tones of shortened duration 92, where the tones are still of sufficient duration to enable that the codes be resolved. This duration enables resolution of returns 93, 94 from object A 88 and object B 89 as shown on the comparative time line. Received signal samples from object A 88 would be acquired in a time interval 99 that was completely separate from the time interval 100 over which received signal samples from object B 89. This duration is still much greater than simple pulse systems, since resolving between these well separated objects 88, 89 requires resolution that is much inferior to resolurion needed for imaging.

Thus, a significant use is made of the capability to limit the time duration of the frequency tones. Tone duration now defines a short field of view for that given tone. There are now multiple sub fields of view that cover the desired, full field of view. This is called bracket gating.

Bracket gating is utilized in conjunction with focal zone effects. Where a focal zone is a beam segment and a collection of such beam segments are coded.

The time duration of a coding tone is matched with a sampling window. In FIG. 17, the transmission 92 is programmed as a composite signal burst that contains many simultaneous tones. Now, if the sampling window 99 is set to center on a single range point, it will only capture reflections from that range. Coded beam segments can be arranged under this system where codes are associated with respective angles, but all codes are for equal ranges. This time window has a time duration that exactly matches the time duration of the tone signal that reflects from that single range. It progressively rejects signals that are at differing ranges so another window 94 is needed to look at other ranges. For ranges where the reflected tone is entirely outside the sampling time window, rejection is very strong. This sets boundaries on the range extent that must be further resolved by the step chirp system. It means that the unambiguous range extent that must be resolved by the step chirp is limited and this limits the number of step chirp steps that must be used.

A staggered transmission method is another feature that is needed to enable efficient bracket gating for situations where simultaneous beam segments are to be acquired from varying ranges. For long tones it is relatively easy to capture a sufficient portion of all tones from multiple range focal zones in a common sampling window. In this situation, a single code sorting process can be used. As tones get shorter and the window gets shorter most of the tones are for a range where reflections do not arrive at a time that fits in a window. Only one tone fits. The staggered burst method solves this problem because timing of transmit tones is arranged so that all tones arrive with best possible overlap in a single sampling window. Signal tones intended for the longer ranges go out first and transmissions of successively shorter range signals are delayed appropriately. This still involves substantial simultaneity and overlapping of tones, but the burst is staggered such that the earliest tones do not overlap with the latest tones. This can still be considered a single burst transmission in the sense that all tones are transmitted prior to waiting for the round trip propagation time.

Staggered, coded transmissions allow efficient, signal sample window operations. This is also shown in FIG. 17 with comparative time lines 111 showing a staggered arrangement where a code is transmitted under a first envelope 92 for object A 88 and another code is transmitted under a second envelope 95 for object B 89. Both codes are reflected 93, 96 from object A 88 and both codes are reflected 94, 97 from object B 89. Noting that these are all on the same wire, the reflection 93 from object A 88 and the reflection 97 from object B 89 arrive at the same time and a sequence of samples that is a sample window 101 acquires both reflected signals. This is important for frequency domain processing because this sample window can be processed by a single FFT operation to extract multiple signals. This is called staggered burst operation.

The transmit beam segment arrangement 27 of FIG. 4 illustrates the usefulness of the staggered burst method. A full planar slice through a field of view is accomplished by this arrangement, but because of the staggered burst and the transmit coding system, the reflected signals are all acquired in a single sampling window.

For large arrays there is still the need for multiple receive windows because outer elements see arrivals from the wide field of view that are more spread out in time. All possible signal paths from each transmit element, to all points in the field, and back to each receive element are accommodated by the system. A system of multiple windows is represented by three different time intervals 102, 102, 103 shown in FIG. 17. This multiple window system is important to give good resolution of the codes. A full system method of implementing the multiple windows is shown in FIG. 23.

The staggered burst, bracket gating operates like a pulse system to give range resolution that controls clutter, but a step chirp method effectively carries out the final range resolving function. Step chirp involves successive tones that operate in frequency steps that sequentially move through the available system band. The duration of the individual tones is sufficiently long to enable an amplitude and phase measurement relative to a reference, yet sufficiently to restrict the range extent over which signals are sampled. Thus, the bracket gate, the focal zone width, the coding system, and the step chirp sequence are all intricately involved in this hybrid mode of operation. These system concepts are discussed in more detail later in this disclosure.

It might seem that this hybrid accomplishes little or nothing compared with simple pulse operations, since time saved with the coding is lost because of time required for the step-chirp steps. There is also a reduction in individual code signal level to allow multiple codes to be transmitted through amplifiers without causing non-linear mixing effects and this reduces signal to noise ratio. The acquisition time is comparable, but the benefit turns out to be noise reduction from narrow band reception effects and integration gain from coherent combinations of the step-chirp signal processing and the total benefit is greater than the loss from the code signal level reduction. This enables deeper penetration in highly attenuating media.

This program of transmit signals also accommodates the need for frequency compensation for different codes that have different rates of attenuation due to their different code frequencies. It also compensates for different attenuation for different depth of each respective tone. FIG. 19 illustrates a spectrum shape 121 that guides the code amplitude adjustments for different depths. This spectrum shape is for the slice mode arrangement of transmit beam segments shown in FIG. 4.

There are many possible beam transmission programs. A cross-range option involves beams that cover a complete planar section of the field of view. This will result in all reflections of interest coming back at about the same time, so all transmit beam codes can be captured in a single sequence of samples and processed as a single sampling window. This can be done in fractional sets to match the sub-array switching options. Again, for the larger arrays, this must be modified with multiple windows for the outer receive elements.

Another coding format that is useful where all codes are used for the same range, but at different angles, is to repeat burst transmission and reception cycles, except the number of repetitions is increased with greater depth. This also aids in deep penetration imaging without excessively prolonging acquisition time.

The step chirp method is overlaid on the transmit beam coding process. This overlaying arrangement involves two different frequency scales. The tones that are codes are defined on the first scale. The tones are transmitted in one burst. The steps of the step chirp are defined on the second scale. These are transmitted sequentially. However, the burst of tones is shifted in frequency on the steps of the step chirp scale. Together, these scales must fit into the available system bandwidth. However, at a given time, a reduced system bandwidth can be imposed in the receiver system that is adequate for one burst of tones. This is done with a multi-channel heterodyne process that uses a sequentially stepped local oscillator that keeps the same signal spectrum for all steps of the step chirp. This is like tuning a common AM radio receiver so that music bandwidth fits into the available intermediate frequency bandwidth. The reception of a burst is then completed with an FFT process that sorts the tone codes by creating parallel channels for respective codes. For common AM radio, this would be the process that the human ear implements. This invention does not de-modulate like AM radio receivers.

For a given tone at a given step, there is a single complex signal sample required. The step chirp signal processor then applies another FFT process to convert from the frequency domain to the time domain. The result for a given tone, is a time function that is the same as if a simple short pulse had been used. This is a synthetic method of creating that short pulse performance.

There is a further type of frequency compensation that is appropriate for deep penetration in highly attenuating media. It also is a variable function depending on depth. A simple pulse is greatly distorted by propagation through the filter effect of the propagation path. This filter reduces the frequency content of the signal to the low frequencies, thereby reducing the bandwidth. This has the effect of greatly extending the pulse width, and limiting its effectiveness in clutter reduction. For simple pulse mode of operation, this is done by transmit signal compensation where a sequence of signal samples is generated with greatly amplified higher frequency components. This requires that an extended time duration signal be programmed, to be stored and transmitted so that a well shaped, short pulse is ultimately received. For step chirp operation, the frequency compensation is simply accomplished by programming a higher level of signal tone amplitude for the higher frequency steps. This keeps uniform signal to noise ratio over the band and a nearly ideal pulse shape can be extracted by signal processing. In either mode, compensation can be done after reception, except that amplified noise is introduced in the process.

FIG. 19 illustrates the compensation for different attenuation for different frequency steps 117 as well as the compensation for different attenuation for different code frequencies 115. The heavy bars 120 are representative of emphasis in dB that is to be added for making penetration effective at the different depths 114. These heavy bars 120 also make the step chirp method effective in forming sharply defined pulses in the process that converts from frequency domain to time domain. Representative spectral shapes 121, 112, 113 are shown for different steps of the step chirp. For pulse systems, the capability to maintain well shaped pulses requires similar spectrum modification prior to transmission of the pulses.

FIG. 19 is also a good representation of the double frequency scale system that is required for the frequency codes 115 and the frequency steps 116.

An alternate mode of operation involves a gated continuous wave method. This is a variation on the bracket gate that extends the continuous wave time extent over multiple short pulses while retaining certain short pulse advantages to accomplish a similar effect as the bracket gate. This method is useful for Doppler velocity sensing. In the coded form of this method, the staggered transmission concept is similarly useful.

Different signal arrangements are needed for Doppler sensing in the coded system. It involves spacing the transmit codes such that there is room for frequency shifted signals to be received and recognized. However, it is not very sensitive because the individual tones are much too broad band to resolve very small Doppler frequency shifts. Here the design utilizes short pulse methods in a different kind of combination. This combination forms very narrow band codes by using a continuous carrier frequency that is turned on and off by a short pulse on and off times. This method is called gated c-w. Such codes are formed by using a continuous carrier of a different frequency.

The range resolution is then dependent on the short pulse duration. Additional codes are spaced at a frequency separation that is the inverse of the short pulse time duration. They can also be spaced more closely at a frequency separation that is an integer multiple of the inverse of the total duration of the signal sequence, where the integer is greater than one. Larger integers give more room for Doppler frequency shift, but there is a limit that is half the pulse repetition frequency.

FIG. 18 shows the time domain and frequency domain relationships for gated c-w methods. Time durations T1 404, T2 405 and T3 406 determine the frequency bands F1 411, F2 410, and F3 409 respectively. The relationships are all according to the formula that frequency band is one divided by the time duration. The continuous wave reference 420 shown is a reference for a single code. Array arrangements with the field of view are the same as previously discussed for FIG. 17. A single code pulse transmission sequence 400 gives rise to reflection sequences 401, 402 from objects A 88 and B 89 on comparative time lines. The short gate 403 timing works as a corresponding time sequence. Instead of analog multiplication with the reference c-w signal over the on time of the gate, a signal digital sample is acquired in that time. This digital sample is multiplied by a coefficient that is pre-computed to represent the reference c-w signal at that time.

Stagger of coded transmissions would involve multiple offset sequences where the sequence 400 is a single member. Following staggered pulses are indicated 416 after the first, in the manner that stagger is shown on the comparative time lines 111 of FIG. 17, except this would be a repetitive event over the duration of T3 406. Staggering would allow the same slice format beam coding that was discussed for the basic tone system.

There are non-useful harmonics determined by the pulse repetition frequency. The Doppler frequency resolution is the inverse of total duration of the multi-pulse sequence. Signal to noise ratio can be improved by increasing individual pulse duration and using the step-chirp process if sharp range resolution is needed. However, this becomes a longer duration process, which may make the velocity sensing inaccurate. Software control, with menu driven commands, enables much flexibility in selection of operating parameters.

With any kind of gated c-w operations, phase lock is required over successive signal bursts relative to a continuous c-w signal. Codes must be locked to their respective continuous c-w signal.

The gated c-w has been an analog function in the past. Digital adaptations sample after the multiplication of the return signal and the continuous carrier reference. However, a new approach used here is to handle the multiplication in the digital domain using samples of the continuous carrier reference, except the samples are not actually made. Rather they are computed coefficients that are the same for all operations. The sequence of transmissions are also computed waveforms.

Injection of reflection enhancing substances into the blood stream allows viewing of deep objects. This process includes monitoring as the substances propagate through the circulation paths. This will see circulation problems with associated implications of disease processes at significant depths. Doppler velocity sensing is especially enhanced by such substances. It is possible that the mixing effects will also be enhanced adjacent to blood flow paths.

Leaving Doppler sensing, gated c-w can be used for extremely difficult, stationary, imaging cases. The pulse can be made as short as required to limit clutter and repeated as many times as necessary to get adequate signal to noise ratio. The filters can be made more and more narrow. Step chirp can then be added to further reduce the range resolution.

Coherent integration of successive signals is a very useful way to improve deep penetration performance. This mode only requires repetition of a transmit and receive cycle where the repeated cycles overlap with exact preservation of relative timing. This does not require the continuous c-w reference. Here the advantage of a flexible system means programs can be written for transmission and receive sequence such that time need not be wasted repeating signals for short range imaging. A gradually increasing number of repetitions will bring the longer range signal to noise ratio up, as appropriate for the varying attenuation.

FIG. 1 shows a receive transducer 3 for a modulation system configuration. The physical arrangement is otherwise the same as the primary mode system. Both arrays of the basic configuration are used for transmitting multiple coded beams. Codes are simple constant frequency tones that are arranged so that the difference frequencies do not overlap in the received signal spectrum. Spacing of codes in the spectrum is a frequency that is the inverse of the tone time duration. This enables efficient signal processing that indicates location of scattering, that is to say more precisely, sources of mixing effects that arise from tissue response non-linearities.

A great variety of intersections can be arranged utilizing the transmit coding method though difference frequencies must be unique for each respective intersection. A transducer receiving signals operates over the band occupied by difference frequencies and code sorting processes form code channels that associate with respective intersections. This gives the orthogonal resolution benefits as before, along with lower frequency benefits and diagnostic benefits. Step chirp methods are applicable for fine grain range resolution. This use of modulation effects requires an electronic capability to switch such that both transducers transmit signals. Signal generation capabilities involving expanded hardware are required for this mode of operation because double the number of channels are needed to provide signal histories to both sets of transducers in the two transducer arrays that now transmit. Receive beamforming functions are eliminated in this mode, with coded transmit beam segments from each array providing the cross range resolution functions and the focal zone control functions.

Signal processing is described here in detail for the basic imaging mode. This includes the rectangularly collimated, wide array apparatus, with coded simultaneous transmit beam segments, simultaneous receive beam segments, staggered bracket gating, step chirp, and plural window, with aberration adjustment, operations. The variety of array forms and signal system modes that can be programmed are extensions of the basic imaging mode that can be accomplished based on this model.

FIG. 20 illustrates representative major hardware components. A 256 element transmit array 210 and a 256 element receive array 200 are shown connected to a first stage computer console 211. This console produces the transmit signals and does the first stage processing of the received signals. The first stage computer console includes 48 computer boards with plug in expansion cards that perform digital to analog conversion for transmit signals and analog to digital conversion for receive signals. First stage processing includes the code sorting FFT operations and the step chirp conversion from frequency domain to time domain FFT operations. The second stage computer console 212 carries out the receive beamforming operations. This second stage computer console includes 16 computer boards for the receive beamforming operations. The first stage computer boards are connected to the second stage computer boards with Ethernet technology centered on the Hewlett Packard network switch 213, the ProCurve 4000. This allows high speed parallel transfer of signals. The second stage computer console 212 also provides 8 more computer boards for image processing functions, control functions, and driving of the display 209. Computer boards are 500 MHz dual Pentium III boards with 10/100 Ethernet port connections. Each computer board has a respective hard disk attached that contain large sets of transmit signals. This hardware has flexibility to handle the varied, general functions discussed in this disclosure. With appropriate adapter devices, such as switches for sub-elements of FIG. 11 and for mosaic switching of FIG. 16, this accommodates all the plug-in transducer array devices.

The general signal processing functions are discussed in reference to FIG. 21. In this figure, three dimensional signal data matrices are shown as blocks. These blocks represent three dimensional mathematical arrays of complex numbers, each part of the complex number being a 16 bit integer. The arrangement shown is for a single slice imaging so the number arrays are shown with the dimensions required for a 256×256 slice image form. A three dimensional imaging system involves 256 of the operations described here. The transformations indicated by the heavy solid lines convert from one block to the next.

Transmit operations utilize programmed signal samples 301 that drive a transmit array 210 via hardware operations 320. A sequence of 1600 samples is required for each of 256 transmit transducer elements for each of 128 steps of the step chirp.

Receive operations utilize signals from the 256 receive transducers 200. The matrix 201 is a complicated matrix form that can be seen as 8 block matrices. The matrix 201 holds varying numbers of samples, to accommodate multiple window requirements, for all 256 receive transducer elements, for all 128 steps of the step chirp process. Transformations indicated by heavy, solid lines 322, 321 and intermediate matrices 300 convert to a two dimensional image data matrix that drives a display 209 via interface operations 225.

The primary operating mode uses simultaneous transmit beamforming and simultaneous receive beamforming. To accomplish this a system of codes is required. Each transmit beam is associated with a code and all codes are transmitted in a staggered, overlapping, sequence collectively as a burst event. Codes are generated by computer, as instructed by software, and stored in special memory devices which can be read out in parallel during a transmission event.

After signal reception, the transmit beams are sorted out according to their respective codes. In the preferred embodiment these codes are simple, discrete frequency values which are sorted by simple filtering in a multiple channel filter, which is implemented using FFT methods.

The receive beamforming is a spatial filtering process, also multiple channels. In some configurations the FFT process can produce, or partially produce, the receive beams as an efficient single transform operation. This multiple channel process eliminates the need for sequential receive beam scanning to cover the field of view. It operates as if the beams are simultaneous, hence the term virtually simultaneous beamforming. In the very near field, the geometric effects limit the use of the FFT. The slower process of individually adjusting phase of samples is needed. This process is more efficiently used as the last process, after the processes of code sorting and range resolving by the step-chirp processing.

These beamforming process are virtually simultaneous, that is, the computer processes operate in a complex fashion where sequential and parallel operations are done very quickly such that the channels are formed as if simultaneous. The important distinction is that the transmission and reception of acoustic energy do not get repeated in sequential scanning processes that take a great amount of time. This makes it possible to accomplish further operations that would, otherwise, be intolerably time consuming.

Transmit signal programs are configured for each transmit element and for each frequency step of the step-chirp such that timing is correct. Very accurate timing is necessary for beamforming. Transmit signal samples are 35 generated by the computers, as instructed by software, and stored in special memory devices which can be read out in parallel during a transmission event. All transmit elements are driven as parallel channels. The step chirp process requires maintaining of consistent phase references for all signals throughout the chirp sequence. This entails repeated code histories, but the number of such sequences is reduced by phase control of the mixing frequency that is produced by a direct digital synthesis device.

FIG. 24 illustrates the transmit signal hardware functions. The extensions 308, 309, 310 indicate 256 channels like the one shown. Each sequence of quadrature samples that represents a transmit signal is stored in a memory 301, converted to analog form 302, filtered 303, and mixed in an image reject double balanced mixer 305. A local oscillator signal is produced by a direct digital synthesis circuit 304 that has frequency and phase adjustment capability under digital control. Analog Devices part AD9833 accomplishes the frequency synthesis function. The image reject mixers with quadrature signal systems are used to reduce number of samples yet simplify filtering requirements. Linear amplifiers 306, adapted from the amateur radio field, are used along with pre-distortion of signals to compensate in imperfections in amplifier linearity. Four amplifiers are required to operate in parallel to drive the four transducer sub-elements 307. Analog phase shifters 311 are digitally controlled vernier adjustments that enable aberration correction at the sub-element level of detail. Vernier phase adjustment is similar to that described for receive signal hardware below. The phase adjustment capability is part of the sub-element amplifiers 306.

FIG. 25 illustrates the receive signal hardware functions. The extensions 251, 252, 253 indicate 256 channels like the one shown. Receive signals from sub-elements 250, of transducer elements 200 in an array 251, drive parallel low noise amplifiers 258. Sub-element phase adjustment 257 is controlled for aberration correction using analog phase shift methods where capacitance in a circuit is adjusted by a voltage controlled by the digital system. The phase shifting capabilities are integrated in the amplifiers 258. Signals are summed and mixed using image reject mixers and an analog to digital converter is used to create a sequence of quadrature digital samples. This establishes complex number sample sequences such that the remainder of the signal processing is with complex numbers. Analog to digital conversion is accomplished with a 14 bit, 10 MHz device that is the Analog Devices part AD9240. 256 such channels are indicated by the arrays 251, 252, 253.

Receive signal processing then involves an FFT code sorting process, an FFT for conversion to time domain, a bulk delay process that selects the appropriate time sample followed by a complex multiplication that adjusts the phase to cause a more exact delay adjustment needed for receive beamforming. Parallel computers process the samples using FFT operations to process overlapping windows to extract codes. FFT operations are again utilized to convert from frequency domain to time domain. Concatenation to build files of the necessary time samples (range samples) as part of the read out to the next stage of computing.

A high capacity network switch is used to implement the transfer to the next stage computers, with software modification to the standard network process that eliminates check sum and validation. This speeds up transfers and helps keep the computers free for other tasks. A useful model of this switch is the Hewlett Packard, Procurve 4000.

The beamforming operation takes place in the second stage of computers. It requires selection of the appropriate time sample and phase adjustment followed by summation to form a receive beam at a particular angle for a particular time (range) point. Such a receive beam is a channel that contains image signals for a given beam.

FIG. 22 illustrates a lower level of detail that is needed to explain the receive operations. In the first stage of computers, the matrix of data samples 201 is first transformed by the FFT process 222 utilizing coefficient and weighting matrix 205 to sort out the codes that are a dimension of a following matrix 202. Another transformation is included 222 that converts signals from each element, for each code, into a time domain sequence that is shown as a range increment dimension of the same matrix 202. The resulting matrix 202 must now be transferred via the network switch to the next stage of computers.

Usual network protocols are eliminated to handle these signal sequences. An example of a time consuming process that is eliminated is the check sum process. Unlike computer networks, these signal number systems are relatively insensitive to errors. The system links are tested only intermittently.

The communication serves to arrange a new matrix 203 that is distributed in sub matrices that are organized by codes. This means that the part of the matrix that represents codes 0 to 3 goes to one computer board, codes 4 to 7 go to the next computer board, and so on. The beamforming transformations are then carried out as if each code represents a system. 4 beam increments are extracted for each code so the image matrix 204 contains 4 beam increments from each code plane of the prior matrix 203. The transform between these matrices 203, 204 is represented by the solid line 224. This transformation 224 utilizes addresses from an address and coefficient matrix 208 to select the appropriate time domain sample for a given element for a given receive beam. This is a bulk delayed sample. A verner delay adjustment is then applied. This phase adjustment is accomplished using complex number coefficients from the address and coefficient matrix 208. This produces beams that are sensitive regions along a line that is at a particular cross range position. The beam increment dimension is range dimension after these beams are formed. Note that the codes correspond to segments of these beams, hence the terminology, beam segment is appropriate in reference to the codes.

It is necessary to further explain the sliding window, or multiple window processing which accommodates the arrival time variations that are entailed by wide transmit beam segments. The receive beamforming process must carve up a wide transmit beam segment 24 into multiple receive beams 26 as shown in FIG. 5. Reflections from within a transmit beam segment 24 arrive at varying times, depending on the cross range position within the transmit beam segment.

FIG. 23 shows the transformation details necessary to transform a sample matrix 201 into a code and range increment matrix 202. The larger submatrices of the sample matrix 201 are needed to hold longer sample sequences. These are marked 4W, 3W, 2W, and 1W indicating the number of windows needed for that set of 32 elements. The greater detail is shown for a single element from the 4W group. The first transformation 245 utilizes overlapping windows as shown for the single element 241. This spreads the sample matrix for one element 241 into a larger decoded matrix 242 for that element. The codes from the different code windows are the same codes; certain codes are just better quality extractions from certain windows. The spread matrix 242 is shown again 243 with the desired range increments from each code window shown as a clear area with W0, W1, W2, and W3 indicated and the undesirable results being shaded. These preferred extractions are then selected to make the compact matrix 244. This is one element of the assembled matrix 202.

Beams line up with the rectangular field of view edges, so they are at cross range separations from each other rather than angle. The resulting image signals are then selected to give the desired planar slice. Thus a fully rectangular field of view is acquired as a block of signals.

In this example, virtually simultaneous transmit beam segments are utilized to give a slice image of 256 by 256 resolution. The full three dimensional acquisition requires repeating this slice 256 times to obtain about two million voxels. The voxels are called channels.

These channels are memory locations that function much like video memory in common personal computers. The magnitude of the complex number that is in a memory location determines pixel brightness. The image signal processing must convert the three dimensional block of data into a two dimensional form that can be put on a display screen. Image processing is discussed later in this disclosure.

Image processing is a major topic. To accomplish this, 8 more computer boards are included in the second stage of computer hardware. Image processing transformations 225 are shown in FIG. 21 and FIG. 22. For the single slice operation shown, this is a simple video operation that is similar to that used in most personal computers. When the slice is repeated to acquire a three dimensional block of data, the two dimensional matrix 204 becomes a three dimensional matrix. Now the function of these transformations is to convert a three dimensional block of data into a two dimensional presentation.

The benefits of orthosound are not fully realized without extensive use being made of the available three dimensional block of image information. The system enables views as if part of the human body were cut away to show parts underneath. A virtual dissection process is enabled. Unlike xray systems where the entire thickness must be collapsed on a single layer, with orthosound a limited range extent can be viewed where both overlaying and underlaying details can be removed to show only the desired region.

A very important form of display is the visual format display. This is view that sees a transverse section that is perpendicular to the bisector of the angle between the illumination and reflected signal directions. This planar like section can be a single resolved increment in thickness or it can be multiple increments that are processed to show objects in a limited range extent. Arbitrary planes can also be selected from the three dimensional block or a limited acquisition plane can be acquired. The three dimensional capabilities also enable comparisons of image results between successive examinations with this equipment or with other imaging modalities. Tracking software enables automated assistance from the computer in the comparison of successive examination results. Software functions include capabilities to adjust for natural changes and to highlight new conditions by subtraction methods that show differences. This is a strong sensitivity enhancing mode of processing because differences can be detectable, even though individual image signals are lost in a clutter interference background. This works for clutter types of interference background more than for noise types of interference. Format conversions to compare with other imaging modalities are entailed.

Image signals are adjusted for natural physical changes in a patient, subtracted from previous image signals, and differences are displayed. A variety of tracking methods are possible to see changes. Correlation methods enable recognition of matching regions and scale adjustments can be applied to effect adjustments in scale. Image signals are also rendered to enable viewing of three dimensional images on common display screens. This includes such processes as combining multiple, parallel layers using greatest of algorithms or addition algorithms. Surface finding algorithms that find surfaces of connected impedance transitions are used to render images. Impedance contour plots are also created. Three dimensional rendering technology is applicable.

Image data is readily put in format for communicating with collaborating medical experts and the image quality will greatly facilitate the collaborating process.

The above capabilities are integrated in a comprehensive medical system apparatus with integrated capability to arrange image equipment in a variety of configurations, select operating modes, and control parameters to carry out a sequence of detection, diagnostic, and therapeutic procedures. Under menu driven control, software is used on computers to drive mechanisms that position and orient transducer arrays and other components of the medical system. Operating modes are selected. Appropriate parameters are provided by computer analysis of the configuration and signal sequences are generated. Operator inputs are accepted with advisory notices displayed.

All steps, from early detection to cure, can be carried out in a single medical visit.

The most important qualities of the system are the deep penetration capability where high resolution of a three dimensional field of view is accomplished in real time for the variety of medical situations that are encountered.

What is claimed is:

1. A sensing system comprising
   (a) two arrays of transducers, where an array is shaped and operated to form a semi-collimated beam segment, and said semi-collimated beam segment defines boundaries of a field of view in one dimension, and
   (b) said two arrays are in approximate orthogonal arrangement to define said field of view in two dimensions and to resolve said field of view in two dimensions, and
   (c) an array transmits coded signals that radiate through said field of view causing a plurality of coded, semi-collimated, transmit, beam segments to form in transmit regions of said field of view such that said coded signals excite respective said transmit regions, where said transmit regions are at different locations in said field of view, and
   (d) objects in said transmit regions cause reflected signals, and
   (e) reflected signals are received and processed to form code channels that respond to signals from respective said transmit regions.

2. A sensing system according to claim 1 and signal means to transmit a step chirp signal sequence, and signal means to receive and process reflected step chirp signals to resolve a dimension of said field of view.

3. A sensing system according to claim 1 and signal means to transmit a step chirp signal sequence and to receive and process reflected step chirp signals to resolve a dimension of said field of view, where a transmit event for each step of said step chirp signal sequence radiates a set of said coded signals, and each of said coded signal is a short tone, and signal means to arrange staggered transmission of short tones such that signal arrival times overlap in a sampling window and field of view is restricted.

4. A sensing system according to claim 1 and said coded, semi-collimated transmit, beam segments are pulsed, semi-collimated transmit beam segments, and said pulsed, semi-collimated transmit beam segments are sequential operations, and said code channels are a single channel that sequentially responds to signals from respective said transmit regions.

5. A sensing system according to claim 1 where said two arrays of transducers are formed from a mosaic of transducers that is alternately configured for transmitting and for receiving by operation of electric circuitry.

6. A sensing system according to claim 1 where said coded signals are adjusted in amplitude to compensate for variable attenuation effects.

7. A sensing system according to claim 1 and signal means for gated continuous wave operation, where said coded signals are gated continuous wave coded signals that are staggered in time to cause overlap in a sampling window in each period of a sequence of periods.

8. A sensing system according to claim 1 where said two arrays are transmit arrays and signals from said two arrays interact in human tissue to produce signals that are of frequency that is different from frequency of transmitted signals.

9. A sensing apparatus comprising:
   (a) two arrays of transducers where an array is shaped and operated to form a semi-collimated beam segment, and a semi-collimated beam segment defines a field of view in one dimension, and
   (b) said two arrays are arranged to define two dimensions of said field of view and to resolve two dimensions of said field of view, and
   (c) where an array transmits signals that radiate through said field of view causing a plurality of coded, semi-collimated, transmit, beam segments to form in transmit regions of said field of view such that coded signals excite respective said regions, and reflected signals are received and processed to form code channels that respond to signals from respective said transmit regions, and
   (d) signal means to transmit a step chirp signal sequence and to receive and process reflected step chirp signals to resolve a dimension of said field of view.

10. A sensing apparatus according to claim 9 where said two arrays of transducers are formed from a mosaic of transducers that is alternately configured for transmitting and for receiving semi-collimated beams by operation of electric circuitry such that array elements are configured to be uniform strips.

11. A sensing apparatus according to claim 9 where signals of said step chirp signal sequence are short tones, and signal means to process received said step chirp signals to resolve a dimension of said field of view such that field of view is restricted by a gating effect made possible by duration of said short tones.

12. A sensing apparatus according to claim 9 and signal means to vary amplitude of steps of said step chirp signal sequence to compensate for variable attenuation effects.

13. A sensing apparatus according to claim 9 where said two arrays are transmit arrays, and a transducer to receive diagnostic signals where said diagnostic signals have a frequency that is not a frequency of transmitted signals.

14. A sensing apparatus comprising:
  (a) two arrays of transducers where an array is shaped and operated to form a beam segment, and said beam segment is focused in one dimension and wide in another dimension, where width of an array is sufficient such that width of said wide beam segment is defined by geometric rules, and
  (b) said beam segment defines boundaries of a field of view in one dimension, and
  (c) said two arrays are arranged to define boundaries of said field of view and to resolve said field of view in two dimensions, and
  (d) signal means to form a plurality of receive beam segments in respective receive regions of said field of view and to form receive beam channels that respond to signals from respective said receive regions.

15. A sensing apparatus according to claim 14 where an array transmits coded signals that radiate through said field of view causing a plurality of coded, transmit, beam segments to form in regions of said field of view such that said coded signals excite respective said regions, and reflected signals are received and processed to form code channels that respond to signals from respective said regions.

16. A sensing apparatus according to claim 14 and signal means to transmit a step chirp signal sequence and to receive and process reflected step chirp signals to resolve a dimension of said field of view.

17. A sensing apparatus according to claim 14 and signal means to resolve a dimension of said field of view utilizing a pulse of short time duration.

18. An imaging system according to claim 14 where said two arrays of transducers are formed from a mosaic of transducers that is alternately configured for transmitting and for receiving by operation of electric circuitry.

19. A sensing apparatus according to claim 14 and harmonic signal processing.

20. A sensing apparatus according to claim 14 and apparatus to manipulate an array.

21. A sensing apparatus according to claim 14 where said semi-collimated beam segment is rectangularly collimated.

22. A sensing apparatus according to claim 14 where said semi-collimated beam segment is cylindrically collimated.

23. A sensing apparatus according to claim 14 and image processing that enables visual format imaging.

24. A sensing apparatus according to claim 14 and signal processing that enables slice format imaging.

25. A sensing apparatus according to claim 14 where elements in an array are sparsely spaced such that grating lobe effects occur and field of view boundaries suppress an effect of reflections from objects outside said field of view.

26. A sensing apparatus according to claim 14 and signal means to resolve a dimension of said field of view utilizing a pulse of short time duration and signal means to pre-distort a pulse to compensate for effects of attenuation.

27. A sensing apparatus according to claim 14 where beam segment formation is accomplished by a combination of shaping a radiating transducer array surface and adjusting time relationships of signals that drive transducer elements.

28. A sensing apparatus according to claim 14 where said arrays overlap.

29. A sensing apparatus according to claim 14 and signal means for gated continuous wave operation.

30. A sensing apparatus according to claim 14 and signal means for gated continuous wave operation and digital storage of coefficients to represent a continuous wave reference signal.

31. A sensing apparatus according to claim 14 and signal means for gated continuous wave operation with capability to discriminate in frequency of reflected signals to sense Doppler shift effects.

32. A sensing apparatus according to claim 14 and capability to acquire a three dimensional block of image signals, and signal means to arrange two dimensional display views that display image signals along arbitrary surfaces.

33. A sensing apparatus according to claim 14 and capability to acquire successive three dimensional blocks of image signals, and signal means to compare said three dimensional blocks to track development of disease.

34. A sensing apparatus according to claim 14 and a device to inject a contrast enhancing substance into a subject of examination.

35. An imaging system according to claim 14 and apparatus to guide surgical instruments.

36. An imaging system according to claim 14 and apparatus to guide injection instruments.

* * * * *